United States Patent
Sharma

(10) Patent No.: US 10,487,338 B2
(45) Date of Patent: Nov. 26, 2019

(54) TRANSGENIC PLANTS WITH ENHANCED TRAITS

(71) Applicant: Monsanto Technology LLC, St. Louis, MO (US)

(72) Inventor: Chitresh Sharma, Solan (IN)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/532,750

(22) PCT Filed: Dec. 2, 2015

(86) PCT No.: PCT/US2015/063311
§ 371 (c)(1),
(2) Date: Jun. 2, 2017

(87) PCT Pub. No.: WO2016/089934
PCT Pub. Date: Jun. 9, 2016

(65) Prior Publication Data
US 2017/0362603 A1   Dec. 21, 2017

Related U.S. Application Data

(60) Provisional application No. 62/086,930, filed on Dec. 3, 2014.

(51) Int. Cl.
*C12N 15/82* (2006.01)
*A01H 1/02* (2006.01)

(52) U.S. Cl.
CPC ........... *C12N 15/8261* (2013.01); *A01H 1/02* (2013.01); *C12N 15/8218* (2013.01); *C12N 15/8271* (2013.01); *Y02A 40/146* (2018.01)

(58) Field of Classification Search
CPC ................................................. C12N 15/8261
USPC ......................................................... 800/290
See application file for complete search history.

(56) References Cited

U.S. PATENT DOCUMENTS

| | | | |
|---|---|---|---|
| 2004/0031072 A1* | 2/2004 | La Rosa | C07H 21/04 800/278 |
| 2011/0162107 A1* | 6/2011 | Inze | C07K 14/415 800/290 |
| 2012/0137382 A1 | 5/2012 | Repetti et al. | |

OTHER PUBLICATIONS

Falcon-Perez Jm et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
(Li, S et al.) TCP3 Interacts with R2R3-MYB Proteins, Promotes Flavonoid Biosynthesis and Negatively Regulates the Auxin Response in *Arabidopsis thaliana*, The Plant Journal, Nov. 12, 2013, vol. 76, No. 6; pp. 901-913; p. 902, col. 2, paragraph 2; DOI: 10.1111/tpj.12348.

* cited by examiner

*Primary Examiner* — Li Zheng
(74) *Attorney, Agent, or Firm* — Dentons US LLP; Lawrence Lavin

(57) ABSTRACT

This disclosure provides recombinant DNA constructs and transgenic plants having enhanced traits such as increased yield, increased nitrogen use efficiency and enhanced drought tolerance; propagules, progeny and field crops of such transgenic plants; and methods of making and using such transgenic plants. This disclosure also provides methods of producing seed from such transgenic plants, growing such seed and selecting progeny plants with enhanced traits. Also disclosed are transgenic plants with altered phenotypes which are useful for screening and selecting transgenic events for the desired enhanced trait.

15 Claims, No Drawings
Specification includes a Sequence Listing.

US 10,487,338 B2

TRANSGENIC PLANTS WITH ENHANCED TRAITS

CROSS REFERENCE TO RELATED APPLICATIONS

This application is a U.S. National Stage filing under 35 U.S.C. § 371 of International Application No. PCT/US2015/063311 filed 2 Dec. 2015, which claims benefit and priority to U.S. Provisional Application No. 62/086,930 filed on 3 Dec. 2014, which are incorporated herein by reference.

INCORPORATION OF SEQUENCE LISTING

The Sequence Listing accompanying this application is contained within the computer readable file "60804US0001_ST25.txt" submitted electronically and contemporaneously with the filing of this application through the USPTO EFS-Web. The file is 43 KB (measured in MS-Windows), was created on 31 May 2017, and is incorporated herein by reference.

FIELD OF THE INVENTION

Disclosed herein are recombinant DNA constructs, plants having enhanced traits such as increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with enhanced traits.

SUMMARY OF THE INVENTION

In one aspect, the disclosure provides a recombinant DNA construct comprising a heterologous promoter functional in a plant cell and operably linked to:
  a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-5;
  b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to SEQ ID NO. 11;
  c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6-10, 15 and 16; or
  d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 12 and 17.

In another aspect, the disclosure provides a suppression recombinant DNA construct that transcribes into a double-stranded RNA, an antisense RNA, a miRNA or a ta-siRNA.

In another aspect, the disclosure provides a suppression recombinant DNA construct that transcribes into a miRNA precursor that produces a mature miRNA having a nucleic acid sequence with at least 95%, at least 96%, at least 97%, at least 98%, at least 99%, or 100% identity to a fragment of at least 19, 20, 21, 22, 23, 24, 25, 26 or 27 consecutive nucleotides of SEQ ID NO. 11.

In another aspect, the disclosure provides a suppression recombinant DNA construct that transcribes into a miRNA precursor that produces a mature miRNA having a nucleic acid sequence with at least 95%, at least 96%, at least 97%, at least 98%, at least 99%, or 100% complimentarity to a fragment of at least 19, 20, 21, 22, 23, 24, 25, 26 or 27 consecutive nucleotides of SEQ ID NO. 11.

In another aspect, the disclosure provides a suppression recombinant DNA construct that transcribes into a miRNA precursor that produces a mature miRNA having a nucleic acid sequence with 100% identity or 100% complementarity to a fragment of 21 consecutive nucleotides of SEQ ID NO. 11.

In another aspect, the disclosure provides a suppression recombinant DNA construct comprising SEQ ID NO. 13.

In another aspect, the disclosure provides a plant comprising a recombinant DNA construct comprising a heterologous promoter functional in a plant cell and operably linked to:
  a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-5;
  b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to SEQ ID NO. 11;
  c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6-10, 15 and 16; or
  d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 12 and 17.

In another aspect, the disclosure provides a plant comprising a recombinant DNA construct of the present disclosure, and having at least one altered phenotype or at least one enhanced trait as compared to a control plant. Such phenotype is characterized or measured by anthocyanin content, biomass, canopy area, chlorophyll content, plant height, water applied, or water use efficiency. Such enhanced trait is increased yield, increased nitrogen use efficiency, or increased water use efficiency.

In another aspect, the disclosure provides a plant comprising a recombinant DNA construct of the present disclosure, wherein the plant is a progeny, a propagule, or a field crop.

In another aspect, the disclosure provides a field crop comprising a recombinant DNA construct of the present disclosure, wherein the field crop is selected from the group consisting of corn, soybean, cotton, canola, rice, barley, oat, wheat, turf grass, alfalfa, sugar beet, sunflower, quinoa and sugar cane.

In another aspect, the disclosure provides a propagule comprising a recombinant DNA construct the present disclosure, wherein the propagule is selected from the group consisting of cell, pollen, ovule, flower, embryo, leaf, root, stem, shoot, meristem, grain and seed.

In another aspect, the disclosure provides a plant comprising a recombinant DNA construct of the present disclosure, wherein the plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, *Miscanthus* plant, pampas grass plant, switchgrass (Panicum) plant, and/or teosinte plant, or is a member of the family Alliaceae, onion plant, leek plant, garlic plant; or wherein the plant is a dicot plant or is a member of the family Amaranthaceae, spinach plant, quinoa plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, papaya plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, eucalyptus plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, *Capsicum* plant, tobacco plant, tomatillo plant, eggplant plant, *Atropa belladona* plant, *Datura stramonium* plant, a member of the family Vitaceae, grape plant, a member of the family Umbelliferae, carrot plant, or a member of the family Musaceae, banana plant; or wherein the plant is a member of the family Pinaceae, cedar plant, fir plant, hemlock plant, larch plant, pine plant, or spruce plant.

In another aspect, the disclosure provides a method for increasing yield, increasing nitrogen use efficiency, or increasing water use efficiency in a plant comprising producing a plant comprising a recombinant DNA construct comprising a heterologous promoter functional in a plant cell and operably linked to:

a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-5;

b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to SEQ ID NO. 11;

c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6-10, 15 and 16; or d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 12 and 17.

In another aspect, the disclosure provides a method for producing a plant by transforming a plant cell or tissue with the recombinant DNA construct of the present disclosure and regenerating a plant from said cell or tissue containing said recombinant DNA construct. In another aspect, the disclosure provides a method for producing a plant by crossing said plant through breeding with:

a) itself;
b) a second plant from the same plant line;
c) a wild type plant; or
d) a second plant from a different line of plants to produce a seed, growing said seed to produce a plurality of progeny plants; and selecting a progeny plant with increased yield, increased nitrogen use efficiency, or increased water use efficiency as compared to a control plant.

DETAILED DESCRIPTION OF THE INVENTION

In the attached sequence listing:

SEQ ID NOs 1 to 5 are nucleotide sequences of the coding strand of the DNA used in the recombinant DNA constructs imparting an enhanced trait in plants, each representing a coding sequence for a protein.

SEQ ID NOs 6 to 10 are amino acid sequences of the cognate proteins of the DNA molecules with nucleotide sequences of SEQ ID NOs 1 to 5 respectively in the same order.

SEQ ID NO. 11 is a nucleotide sequence representing a coding sequence of a suppression target gene.

SEQ ID NO. 12 is an amino acid sequence of the cognate protein of the DNA molecule with nucleotide sequence of SEQ ID NO. 11.

SEQ ID NO. 13 is a nucleotide sequence of DNA molecule used in the recombinant DNA construct imparting an enhanced trait or altered phenotype in plants, representing an engineered miRNA precursor sequence.

SEQ ID NO. 14 is a nucleotide sequence of the target recognition site of the engineered miRNA precursor with nucleotide sequence of SEQ ID NO. 13.

SEQ ID NOs 15, 16 and 17 are amino acid sequences of proteins homologous to the proteins with amino acid sequences of SEQ ID NOs 6, 9 and 12 respectively in the same order.

SEQ ID NOs 18 to 21 are nucleotide sequences of variants of a rice MIR gene.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotide of the DNA with uracil (U) nucleotide. Thus, providing a specific DNA sequence is understood to define the exact RNA equivalent. A given first polynucleotide sequence, whether DNA or RNA, further defines the sequence of its exact complement (which can be DNA or RNA), i. e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. A first nucleic acid sequence is "operably" connected or "linked" with a second nucleic acid sequence when the first nucleic acid sequence is placed in a functional relationship with the second nucleic acid sequence. For example, a promoter sequence is "operably linked" to DNA if the promoter provides for transcription or expression of the DNA. Generally, operably linked DNA sequences are contiguous.

As used herein, the term "expression" refers to the production of a polynucleotide or a protein by a plant, plant cell or plant tissue which can give rise to an altered phenotype or enhanced trait. Expression can also refer to the process by which information from a gene is used in the synthesis of functional gene products, which may include but are not limited to other polynucleotides or proteins which may serve, e.g., an enzymatic, structural or regulatory function. Gene products having a regulatory function include but are not limited to elements that affect the occurrence or level of transcription or translation of a target protein. In some cases, the expression product is a non-coding functional RNA.

"Modulation" of expression refers to the process of effecting either overexpression or suppression of a polynucleotide or a protein.

The term "suppression" as used herein refers to a lower expression level of a target polynucleotide or target protein in a plant, plant cell or plant tissue, as compared to the expression in a wild-type or control plant, cell or tissue, at any developmental or temporal stage for the gene. The term "target protein" as used in the context of suppression refers to a protein which is suppressed; similarly, "target mRNA" refers to a polynucleotide which can be suppressed or, once expressed, degraded so as to result in suppression of the target protein it encodes. The term "target gene" as used in the context of suppression refers to either "target protein" or "target mRNA". In alternate non-limiting embodiments, the target protein or target polynucleotide is one the suppression of which can give rise to an enhanced trait or altered phenotype directly or indirectly. In one exemplary embodiment, the target protein is one which can indirectly increase or decrease the expression of one or more other proteins, the increased or decreased expression, respectively, of which is associated with an enhanced trait or an altered phenotype. In another exemplary embodiment, the target protein can bind to one or more other proteins associated with an altered phenotype or enhanced trait to enhance or inhibit their function and thereby affect the altered phenotype or enhanced trait indirectly.

Suppression can be applied using numerous approaches. Non limiting examples include: suppressing an endogenous gene(s) or a subset of genes in a pathway, suppressing one or more mutation that has resulted in decreased activity of a protein, suppressing the production of an inhibitory agent, to elevate, reducing or eliminating the level of substrate that an enzyme requires for activity, producing a new protein, activating a normally silent gene; or accumulating a product that does not normally increase under natural conditions.

Conversely, the term "overexpression" as used herein refers to a greater expression level of a polynucleotide or a protein in a plant, plant cell or plant tissue, compared to expression in a wild-type plant, cell or tissue, at any developmental or temporal stage for the gene. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "target protein" as used herein in the context of overexpression refers to a protein which is overexpressed; "target mRNA" refers to an mRNA which encodes and is translated to produce the target protein, which can also be overexpressed. The term "target gene" as used in the context of overexpression refers to either "target protein" or "target mRNA". In alternative embodiments, the target protein can effect an enhanced trait or altered phenotype directly or indirectly. In the latter case it may do so, for example, by affecting the expression, function or substrate available to one or more other proteins. In an exemplary embodiment, the target protein can bind to one or more other proteins associated with an altered phenotype or enhanced trait to enhance or inhibit their function.

Overexpression can be achieved using numerous approaches. In one embodiment, overexpression can be achieved by placing the DNA sequence encoding one or more polynucleotides or polypeptides under the control of a promoter, examples of which include but are not limited to endogenous promoters, heterologous promoters, inducible promoters and tissue specific promoters. In one exemplary embodiment, the promoter is a constitutive promoter, for example, the cauliflower mosaic virus 35S transcription initiation region. Thus, depending on the promoter used, overexpression can occur throughout a plant, in specific tissues of the plant, or in the presence or absence of different inducing or inducible agents, such as hormones or environmental signals.

Gene Suppression Elements: The gene suppression element can be transcribable DNA of any suitable length, and generally includes at least about 19 to about 27 nucleotides (for example 19, 20, 21, 22, 23, or 24 nucleotides) for every target gene that the recombinant DNA construct is intended to suppress. In many embodiments the gene suppression element includes more than 23 nucleotides (for example, more than about 30, about 50, about 100, about 200, about 300, about 500, about 1000, about 1500, about 2000, about 3000, about 4000, or about 5000 nucleotides) for every target gene that the recombinant DNA construct is intended to suppress.

Suitable gene suppression elements useful in the recombinant DNA constructs of the invention include at least one element (and, in some embodiments, multiple elements) selected from the group consisting of:

(a) DNA that includes at least one anti-sense DNA segment that is anti-sense to at least one segment of the at least one first target gene; (b) DNA that includes multiple copies of at least one anti-sense DNA segment that is anti-sense to at least one segment of the at least one first target gene; (c) DNA that includes at least one sense DNA segment that is at least one segment of the at least one first target gene; (d) DNA that includes multiple copies of at least one sense DNA segment that is at least one segment of the at least one first target gene; (e) DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene; (f) DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene; (g) DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats; (h) DNA that includes nucleotides derived from a miRNA, preferably a plant miRNA; (i) DNA that includes nucleotides of a siRNA; (j) DNA that transcribes to an RNA aptamer capable of binding to a ligand; and (k) DNA that transcribes to an RNA aptamer capable of binding to a ligand, and DNA that transcribes to regulatory RNA capable of regulating expression of the first target gene, wherein the regulation is dependent on the conformation of the regulatory RNA, and the conformation of the regulatory RNA is allosterically affected by the binding state of the RNA aptamer.

Any of these gene suppression elements, whether transcribing to a single double-stranded RNA or to multiple double-stranded RNAs, can be designed to suppress more than one target gene, including, for example, more than one allele of a target gene, multiple target genes (or multiple segments of at least one target gene) from a single species, or target genes from different species.

Anti-Sense DNA Segments: In one embodiment, the at least one anti-sense DNA segment that is anti-sense to at least one segment of the at least one first target gene includes DNA sequence that is anti-sense or complementary to at least a segment of the at least one first target gene, and can include multiple anti-sense DNA segments, that is, multiple copies of at least one anti-sense DNA segment that is anti-sense to at least one segment of the at least one first target gene. Multiple anti-sense DNA segments can include DNA sequence that is anti-sense or complementary to multiple segments of the at least one first target gene, or to multiple copies of a segment of the at least one first target gene, or to segments of multiple first target genes, or to any combination of these. Multiple anti-sense DNA segments can be fused into a chimera, e.g., including DNA sequences that are anti-sense to multiple segments of one or more first target genes and fused together.

The anti-sense DNA sequence that is anti-sense or complementary to (that is, can form Watson-Crick base-pairs with) at least a segment of the at least one first target gene has at least about 80%, or at least about 85%, or at least about 90%, or at least about 95% complementarity to at least a segment of the at least one first target gene. In one embodiment, the DNA sequence that is anti-sense or complementary to at least a segment of the at least one first target gene has between about 95% to about 100% complementarity to at least a segment of the at least one first target gene. Where the at least one anti-sense DNA segment includes multiple anti-sense DNA segments, the degree of complementarity can be, but need not be, identical for all of the multiple anti-sense DNA segments.

Sense DNA Segments: In another embodiment, the at least one sense DNA segment that is at least one segment of the at least one first target gene includes DNA sequence that corresponds to (that is, has a sequence that is identical or substantially identical to) at least a segment of the at least one first target gene, and can include multiple sense DNA segments, that is, multiple copies of at least one sense DNA segment that corresponds to (that is, has the nucleotide sequence of) at least one segment of the at least one first target gene. Multiple sense DNA segments can include DNA sequence that is or that corresponds to multiple segments of the at least one first target gene, or to multiple copies of a segment of the at least one first target gene, or to segments of multiple first target genes, or to any combination of these. Multiple sense DNA segments can be fused into a chimera, that is, can include DNA sequences corresponding to multiple segments of one or more first target genes and fused together.

The sense DNA sequence that corresponds to at least a segment of the target gene has at least about 80%, or at least about 85%, or at least about 90%, or at least about 95% sequence identity to at least a segment of the target gene. In one embodiment, the DNA sequence that corresponds to at least a segment of the target gene has between about 95% to about 100% sequence identity to at least a segment of the target gene. Where the at least one sense DNA segment includes multiple sense DNA segments, the degree of sequence identity can be, but need not be, identical for all of the multiple sense DNA segments.

Multiple Copies: Where the gene suppression element includes multiple copies of anti-sense or multiple copies of sense DNA sequence, these multiple copies can be arranged serially in tandem repeats. In some embodiments, these multiple copies can be arranged serially end-to-end, that is, in directly connected tandem repeats. In some embodiments, these multiple copies can be arranged serially in interrupted tandem repeats, where one or more spacer DNA segment can be located adjacent to one or more of the multiple copies. Tandem repeats, whether directly connected or interrupted or a combination of both, can include multiple copies of a single anti-sense or multiple copies of a single sense DNA sequence in a serial arrangement or can include multiple copies of more than one anti-sense DNA sequence or of more than one sense DNA sequence in a serial arrangement.

Double-stranded RNA: In those embodiments wherein the gene suppression element includes either at least one anti-sense DNA segment that is anti-sense to at least one segment of the at least one target gene or at least one sense DNA segment that is at least one segment of the at least one target gene, RNA transcribed from either the at least one anti-sense or at least one sense DNA may become double-stranded by the action of an RNA-dependent RNA polymerase. See, for example, U.S. Pat. No. 5,283,184, which is incorporated by reference herein.

In yet other embodiments, the gene suppression element can include DNA that transcribes to RNA for suppressing the at least one first target gene by forming double-stranded RNA and includes at least one anti-sense DNA segment that is anti-sense to at least one segment of the at least one target gene (as described above under the heading "Anti-sense DNA Segments") and at least one sense DNA segment that is at least one segment of the at least one first target gene (as described above under the heading "Sense DNA Segments"). Such a gene suppression element can further include spacer DNA segments. Each at least one anti-sense DNA segment is complementary to at least part of a sense DNA segment in order to permit formation of double-stranded RNA by intramolecular hybridization of the at least one anti-sense DNA segment and the at least one sense DNA segment. Such complementarity between an anti-sense DNA segment and a sense DNA segment can be, but need not be, 100% complementarity; in some embodiments, this complementarity can be preferably at least about 80%, or at least about 85%, or at least about 90%, or at least about 95% complementarity.

The double-stranded RNA can be in the form of a single dsRNA "stem" (region of base-pairing between sense and anti-sense strands), or can have multiple dsRNA "stems". In one embodiment, the gene suppression element can include DNA that transcribes to RNA for suppressing the at least one first target gene by forming essentially a single double-stranded RNA and includes multiple serial anti-sense DNA segments that are anti-sense to at least one segment of the at least one first target gene and multiple serial sense DNA segments that are at least one segment of the at least one first target gene; the multiple serial anti-sense and multiple serial sense segments can form a single double-stranded RNA "stem" or multiple "stems" in a serial arrangement (with or without non-base paired spacer DNA separating the multiple "stems"). In another embodiment, the gene suppression element includes DNA that transcribes to RNA for suppressing the at least one first target gene by forming multiple dsRNA "stems" of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of dsRNA "stems" (such as, but not limited to "inverted repeats"). Such multiple dsRNA "stems" can further be arranged in series or clusters to form tandem inverted repeats, or structures resembling "hammerhead" or "cloverleaf" shapes. Any of these gene suppression elements can further include spacer DNA segments found within a dsRNA "stem" (for example, as a spacer between multiple anti-sense or sense DNA segments or as a spacer between a base-pairing anti-sense DNA segment and a sense DNA segment) or outside of a double-stranded RNA "stem" (for example, as a loop region separating a pair of inverted repeats). In cases where base-pairing anti-sense and sense DNA segment are of unequal length, the longer segment can act as a spacer.

miRNAs: In a further embodiment, the gene suppression element can include DNA that includes nucleotides derived from a miRNA (microRNA), that is, a DNA sequence that corresponds to a miRNA native to a virus or a eukaryote of interest (including plants and animals, especially invertebrates), or a DNA sequence derived from such a native miRNA but modified to include nucleotide sequences that do not correspond to the native miRNA. While miRNAs have not to date been reported in fungi, fungal miRNAs, should they exist, are also suitable for use in the invention. An embodiment includes a gene suppression element containing DNA that includes nucleotides derived from a viral or plant miRNA.

In a non-limiting example, the nucleotides derived from a miRNA can include DNA that includes nucleotides corresponding to the loop region of a native miRNA and nucleotides that are selected from a target gene sequence. In another non-limiting example, the nucleotides derived from a miRNA can include DNA derived from a miRNA precursor sequence, such as a native pri-miRNA or pre-miRNA sequence, or nucleotides corresponding to the regions of a native miRNA and nucleotides that are selected from a target gene sequence number such that the overall structure (e.g., the placement of mismatches in the stem structure of the pre-miRNA) is preserved to permit the pre-miRNA to be processed into a mature miRNA. In yet another embodiment, the gene suppression element can include DNA that includes nucleotides derived from a miRNA and capable of inducing or guiding in-phase cleavage of an endogenous transcript into trans-acting siRNAs, as described by Allen et al. (2005) Cell, 121:207-221, which is incorporated by reference in its entirety herein. Thus, the DNA that includes nucleotides derived from a miRNA can include sequence naturally occurring in a miRNA or a miRNA precursor molecule, synthetic sequence, or both.

siRNAs: In yet another embodiment, the gene suppression element can include DNA that includes nucleotides of a small interfering RNA (siRNA). The siRNA can be one or more native siRNAs (such as siRNAs isolated from a non-transgenic eukaryote or from a transgenic eukaryote), or can be one or more DNA sequences predicted to have siRNA activity (such as by use of predictive tools known in the art, see, for example, Reynolds et al. (2004) Nature Biotechnol., 22:326-330, which is incorporated by reference in its entirety herein). Multiple native or predicted siRNA sequences can be joined in a chimeric siRNA sequence for gene suppression. Such a DNA that includes nucleotides of a siRNA includes at least 19 nucleotides, and in some embodiments includes at least 20, at least 21, at least 22, at least 23, or at least 24 nucleotides. In other embodiments, the DNA that includes nucleotides of a siRNA can contain substantially more than 21 nucleotides, for example, more than about 50, about 100, about 300, about 500, about 1000, about 3000, or about 5000 nucleotides or greater.

Engineered miRNAs and trans-acting siRNAs (ta-siRNAs) are useful for gene suppression with increased specificity. The invention provides recombinant DNA constructs, each including a transcribable engineered miRNA precursor designed to suppress a target sequence, wherein the transcribable engineered miRNA precursor is derived from the fold-back structure of a MIR gene, preferably a plant MIR sequence. These miRNA precursors are also useful for directing in-phase production of siRNAs (e.g., heterologous sequence designed to be processed in a trans-acting siRNA suppression mechanism in planta). The invention further provides a method to suppress expression of a target sequence in a plant cell, including transcribing in a plant cell a recombinant DNA including a transcribable engineered miRNA precursor designed to suppress a target sequence, wherein the transcribable engineered miRNA precursor is derived from the fold-back structure of a MIR gene, preferably a plant MIR sequence, whereby expression of the target sequence is suppressed relative to its expression in the absence of transcription of the recombinant DNA construct. In specifically claimed embodiments, the transcribable engineered miRNA precursor is derived from the fold-back structure of a rice MIR sequence selected from the group consisting of SEQ ID NOs. 18-21, and their complements.

The mature miRNAs produced, or predicted to be produced, from these miRNA precursors may be engineered for use in suppression of a target gene, e.g., in transcriptional suppression by the miRNA, or to direct in-phase production of siRNAs in a trans-acting siRNA suppression mechanism (see Allen et al. (2005) Cell, 121:207-221, Vaucheret (2005) Science STKE, 2005:pe43, and Yoshikawa et al. (2005) Genes Dev., 19:2164-2175, all of which are incorporated by reference herein). Plant miRNAs generally have near-perfect complementarity to their target sequences (see, for example, Llave et al. (2002) Science, 297:2053-2056, Rhoades et al. (2002) Cell, 110:513-520, Jones-Rhoades and Bartel (2004) Mol. Cell, 14:787-799, all of which are incorporated by reference herein). Thus, the mature miRNAs can be engineered to serve as sequences useful for gene suppression of a target sequence, by replacing nucleotides of the mature miRNA sequence with nucleotides of the sequence that is targeted for suppression; see, for example, methods disclosed by Parizotto et al. (2004) Genes Dev., 18:2237-2242 and especially U.S. Patent Application Publications US2004/0053411A1, US2004/0268441A1, US2005/0144669, and US2005/0037988 all of which are incorporated by reference herein. When engineering a novel miRNA to target a specific sequence, one strategy is to select within the target sequence a region with sequence that is as similar as possible to the native miRNA sequence. Alternatively, the native miRNA sequence can be replaced with a region of the target sequence, preferably a region that meets structural and thermodynamic criteria believed to be important for miRNA function (see, for example, U.S. Patent Application Publication US2005/0037988). Sequences are preferably engineered such that the number and placement of mismatches in the stem structure of the fold-back region or pre-miRNA is preserved. Thus, an engineered miRNA or engineered miRNA precursor can be derived from any of the mature miRNA sequences, or their corresponding miRNA precursors (including the fold-back portions of the corresponding MIR genes) disclosed herein. The engineered miRNA precursor can be cloned and expressed (transiently or stably) in a plant cell or tissue or intact plant.

The construction and description of recombinant DNA constructs to modulate small non-coding RNA activities are disclosed in US Patent Application Publication US 2009/0070898 A1, US2011/0296555 A1, US2011/0035839 A1, all of which are incorporated herein by reference in their entirety. In particular, with respect to US2011/0035839 A1, see e.g., sections under the headings "Gene Suppression Elements" in paragraphs 122 to 135, and "Engineered Heterologous miRNA for Controlling Gene Expression in paragraphs 188 to 190.

As used herein a "plant" includes a whole plant, a transgenic plant, meristematic tissue, a shoot organ/structure (for example, leaf, stem and tuber), a root, a flower, a floral organ/structure (for example, a bract, a sepal, a petal, a stamen, a carpel, an anther and an ovule), a seed (including an embryo, endosperm, and a seed coat) and a fruit (the mature ovary), plant tissue (for example, vascular tissue, ground tissue, and the like) and a cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular algae.

As used herein a "transgenic plant cell" means a plant cell that is transformed with stably-integrated, recombinant DNA, for example, by *Agrobacterium*-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, for example, into a transgenic plant with stably-integrated, recombinant DNA, or seed or pollen derived from a progeny transgenic plant.

As used herein a "control plant" means a plant that does not contain the recombinant DNA of the present disclosure that imparts an enhanced trait or altered phenotype. A control plant is used to identify and select a transgenic plant that has an enhanced trait or altered phenotype. A suitable control plant can be a non-transgenic plant of the parental line used to generate a transgenic plant, for example, a wild type plant devoid of a recombinant DNA. A suitable control plant can also be a transgenic plant that contains recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isogenic line.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of drought tolerance, increased water use efficiency, cold tolerance, increased nitrogen use efficiency and increased yield as shown in Tables 7 and 8, and altered phenotypes as shown in Tables 4-6. In another aspect of the disclosure the trait is increased yield under non-stress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait as compared to a control plant. It is known that there can be natural variations in a modified trait. Therefore, the trait modification observed entails a change of the normal distribution and magnitude of the trait in the plants as compared to a control plant.

The present disclosure relates to a plant with improved economically important characteristics, more specifically increased yield. More specifically the present disclosure relates to a plant comprising a polynucleotide of this disclosure, wherein the plant has increased yield as compared to a control plant. Many plants of this disclosure exhibited increased yield as compared to a control plant. In an embodiment, a plant of the present disclosure exhibited an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), seed production and more. Root development, photosynthetic efficiency, nutrient uptake, stress tolerance, early vigor, delayed senescence and functional stay green phenotypes can be important factors in determining yield. Optimizing the above mentioned factors can therefore contribute to increasing crop yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear and number of kernels per row, kernel number or weight per ear, weight per kernel, ear number, ear weight, fresh or dry ear biomass (weight).

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kg/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure provides a method for the production of plants having increased yield; performance of the method gives plants increased yield. "Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others.

Further, increased yield can also manifest as (iii) increased total seed yield, which may result from one or more of an increase in seed biomass (seed weight) due to an increase in the seed weight on a per plant and/or on an individual seed basis an increased number of panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds.

Increased yield can also (iv) result in modified architecture, or can occur because of modified plant architecture.

Increased yield can also manifest as (v) increased harvest index, which is expressed as a ratio of the yield of harvestable parts, such as seeds, over the total biomass Increased yield can also manifest as (vi) increased kernel weight, which is extrapolated from the number of filled seeds counted and their total weight. An increased kernel weight can result from an increased seed size and/or seed weight, an increase in embryo size, increased endosperm size, aleurone and/or scutellum, or an increase with respect to other parts of the seed that result in increased kernel weight.

Increased yield can also manifest as (vii) increased ear biomass, which is the weight of the ear and can be represented on a per ear, per plant or per plot basis.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to, seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of increasing yield in a plant by producing a plant comprising a polynucleic acid sequence of this disclosure where the plant can be crossed with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA construct, transgenic plants can be prepared by crossing a first plant having a stably integrated recombinant DNA construct with a second plant lacking the DNA. For example, recombinant DNA can be introduced into a first plant line that is amenable to transformation to produce a transgenic plant which can be crossed with a second plant line to introgress the recombinant DNA into the second plant line.

Selected transgenic plants transformed with a recombinant DNA construct and having the polynucleotide of this disclosure provides the enhanced trait of increased yield compared to a control plant. Use of genetic markers associated with the recombinant DNA can facilitate production of transgenic progeny that is homozygous for the desired recombinant DNA. Progeny plants carrying DNA for both parental traits can be back-crossed into a parent line multiple times, for example usually 6 to 8 generations, to produce a progeny plant with substantially the same genotype as the one reoccurring original transgenic parental line but having the recombinant DNA of the other transgenic parental line. The term "progeny" denotes the offspring of any generation of a parent plant prepared by the methods of this disclosure containing the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, a oligonucleotide, or any fragment thereof. In many instances, a polynucleotide encodes a polypeptide (or protein) or a domain or a fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide.

A "synthetic polypeptide" is a polypeptide created by consecutive polymerization of isolated amino acid residues using methods known in the art.

An "isolated polypeptide", whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, for example, alternatively denoted: 105%, 110%, 120%, 150% or more, enriched relative to wild type standardized at 100%. Such enrichment is not the result of a natural response of a wild-type plant. Alternatively, or additionally, the isolated polypeptide is separated from other cellular components, with which it is typically associated, for example, by any of the various protein purification methods.

As used herein, a "functional fragment" refers to a portion of a polypeptide provided herein which retains full or partial molecular, physiological or biochemical function of the full length polypeptide. A functional fragment often contains the domain(s), such as Pfam domains (see below), identified in the polypeptide provided in the sequence listing.

A "recombinant DNA construct" as used in the present disclosure comprises at least one expression cassette having a promoter operable in plant cells and a polynucleotide of the present disclosure. DNA constructs can be used as a means of delivering recombinant DNA constructs to a plant cell in order to effect stable integration of the recombinant molecule into the plant cell genome. In one embodiment, the polynucleotide can encode a protein or variant of a protein or fragment of a protein that is functionally defined to maintain activity in transgenic host cells including plant cells, plant parts, explants and whole plants. In another embodiment, the polynucleotide can encode a non-coding RNA that interferes with the functioning of endogenous classes of small RNAs that regulate expression, including but not limited to taRNAs, siRNAs and miRNAs. Recombinant DNA constructs are assembled using methods known to persons of ordinary skill in the art and typically comprise a promoter operably linked to DNA, the expression of which provides the enhanced agronomic trait.

Other construct components can include additional regulatory elements, such as 5' leaders and introns for enhancing transcription, 3' untranslated regions (such as polyadenylation signals and sites), and DNA for transit or targeting or signal peptides.

Percent identity describes the extent to which polynucleotides or protein segments are invariant in an alignment of sequences, for example nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence.

An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from common ancestral genes by speciation and encode proteins retain the same function, but do not include paralogs, i.e., genes that are related by duplication but have evolved to encode proteins with different functions. Homologous genes include naturally occurring alleles and artificially-created variants.

Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their corresponding nucleotide sequences, have typically at least about 60% identity, in some instances at least about 70%, at least about 75%, at least about 80%, at least about 85%, at least about 90%, at least about 92%, at least about 94%, at least about 95%, at least about 96%, at least about 97%, at least about 98%, at least about 99%, or even at least about 99.5% identity over the full length of a protein or its corresponding nucleotide sequence identified as being associated with imparting an enhanced trait or altered phenotype when expressed in plant cells. In one aspect of the disclosure homolog proteins have at least about 80%, at least about 85%, at least about 90%, at least about 92%, at least about 94%, at least about 95%, at least about 96%, at least about 97%, at least about 98%, at least about 99%, or at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alaninevaline, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions (UTRs) and their complements. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

Sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252, zein Z27 as disclosed by Russell et al. (1997) *Transgenic Res.* 6(2):157-166, globulin 1 as disclosed by Belanger et al (1991) *Genetics* 129:863-872, glutelin 1 as disclosed by Russell (1997) supra, and peroxiredoxin antioxidant (Per1) as disclosed by Stacy et al. (1996) *Plant Mol Biol.* 31(6):1205-1216.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule. As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, and vacuolar sorting peptides. For description of the use of chloroplast transit peptides see U.S. Pat. Nos. 5,188,642 and 5,728,925. For description of the transit peptide region of an Arabidopsis EPSPS gene in the present disclosure, see Klee, H. J. Et al (MGG (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989.

Expression cassettes of this disclosure can also contain one or more genes that encode selectable markers and confer resistance to a selective agent such as an antibiotic or an herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), U.S. Patent Publication 2009/0138985A1 and gentamycin (aac3 and aacC4) or tolerance to herbicides like glyphosate (for example, 5-enolpyruvyl-shikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011)), bialaphos or phosphinothricin or derivatives (e. g., phosphinothricin acetyltransferase (bar) tolerance to phosphinothricin or glufosinate (U.S. Pat. Nos. 5,646,024; 5,561,236; 5,276,268; 5,637,489; 5,273,894); dicamba (dicamba monooxygenase, Patent Application Publications US2003/0115626A1), or sethoxydim (modified acetyl-coenzyme A carboxylase for conferring tolerance to cyclohexanedione (sethoxydim)), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The term "transgenic plant" refers to a plant comprising such a transgene. The coding region usually codes for a protein of interest but can also code for a functional RNA of interest, for example an antisense RNA, a nontranslated RNA, in the sense or antisense direction, a miRNA, a noncoding RNA, or a synthetic RNA used in either suppression or over expression of target gene sequences. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example a first molecule from one gene or organism and a second molecule from another gene or organism.

Recombinant DNA constructs in this disclosure generally include a 3' element that typically contains a polyadenylation signal and site. Known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication 2002/

0192813 A1; and the pea (*Pisum sativum*) ribulose biphosphate carboxylase gene (rbs 3'), and 3' elements from the genes within the host plant.

As used herein "operably linked" means the association of two or more DNA fragments in a recombinant DNA construct so that the function of one, for example, protein-encoding DNA, is controlled by the other, for example, a promoter.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil and norflurazon herbicides. Polynucleotide molecules encoding proteins involved in herbicide tolerance known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No 5,463,175 and a glyphosate-N-acetyl transferase (GAT) disclosed in US Patent Application Publication 2003/0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in US Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 6,506,599; 5,986,175 and US Patent Application Publication 2003/0150017 A1.

Plant Cell Transformation Methods

Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in U.S. Pat. Nos. 5,015,580 (soybean); 5,550,318 (corn); 5,538,880 (corn); 5,914,451 (soybean); 6,160,208 (corn); 6,399,861 (corn); 6,153,812 (wheat) and 6,365,807 (rice). *Agrobacterium*-mediated transformation methods are described in U.S. Pat. Nos. 5,159,135 (cotton); 5,824,877 (soybean); 5,463,174 (canola); 5,591,616 (corn); 5,846,797 (cotton); 8,044,260 (cotton); 6,384,301 (soybean), 7,026,528 (wheat) and 6,329,571 (rice), US Patent Application Publication 2004/0087030 A1 (cotton), and US Patent Application Publication 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA construct, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

For transformation, DNA is typically introduced into only a small percentage of target plant cells in any one transformation experiment. Marker genes are used to provide an efficient system for identification of those cells that are stably transformed by receiving and integrating a recombinant DNA construct into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708; 6,118,047 and 8,030,544. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}s^{-1}$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an enhanced agronomic trait.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of sequences of protein-encoding genes as recombinant DNA for production of transgenic plants with enhanced traits. The elements of Table 1 are described by reference to:

"NUC SEQ ID NO." which identifies a DNA sequence.
"PEP SEQ ID NO." which identifies an amino acid sequence.
"Gene ID" which refers to an arbitrary identifier.
"Gene Name and Description" which is a common name and functional description of the gene.

TABLE 1

Sequences for Protein-Coding Genes

| NUC SEQ ID NO. | PEP SEQ ID NO. | Gene ID | Gene Name and Description |
|---|---|---|---|
| 1 | 6 | TRDX4M-1 | Arabidopsis Transcription factor TCP3 |
| 2 | 7 | TRDX4M-2 | variant of Arabidopsis B-box 32 gene, with 157-174aa deletion |
| 3 | 8 | TRDX4M-3 | Variant of Arabidopsis ERF/AP2 (ethylene response factor) subfamily B-3 transcription factor, with 46aa-Cterminus truncation |
| 4 | 9 | TRDX4M-4 | Arabidopsis NAM-B1 Homolog; NAC transcription factor 25 |
| 5 | 10 | TRDX4M-5 | Soybean basic helix-loop-helix (bHLH) family protein |

Table 2 provides a list of sequences for suppression of target protein-coding genes, as recombinant DNA for production of transgenic plants with enhanced traits. The elements of Table 2 are described by reference to:

"Target NUC SEQ ID NO." which identifies a nucleotide coding sequence of the suppression target gene.
"Target PEP SEQ ID NO." which identifies an amino acid sequence of the suppression target gene.
"Target Gene ID" which is an arbitrary identifier of the suppression target gene.
"Engineered miRNA precursor SEQ ID NO." which identifies a nucleotide sequence of the miRNA construct.
"miRNA recognition site SEQ ID NO." which identifies a nucleotide sequence of the miRNA recognition site.
"Target Gene Name and Description" which is a common name and functional description of the suppression target gene.

TABLE 2

Sequences for Gene Suppression

| Target NUC SEQ ID NO. | Target PEP SEQ ID NO. | Target Gene ID | Engineered miRNA precursor SEQ ID NO. | miRNA recognition site SEQ ID NO. | Target Gene Name and Description |
|---|---|---|---|---|---|
| 11 | 12 | TRDX4M-1T | 13 | 14 | Corn putative RNF169 interacting protein |

Selection Methods for Transgenic Plants with Enhanced Traits

Within a population of transgenic plants each regenerated from a plant cell with recombinant DNA many plants that survive to fertile transgenic plants that produce seeds and progeny plants will not exhibit an enhanced agronomic trait. Selection from the population is necessary to identify one or more transgenic plants with an enhanced trait. Transgenic plants having enhanced traits are selected from populations of plants regenerated or derived from plant cells transformed as described herein by evaluating the plants in a variety of assays to detect an enhanced trait, for example, increased water use efficiency or drought tolerance, enhanced high temperature or cold tolerance, increased yield, increased nitrogen use efficiency, enhanced seed composition such as enhanced seed protein and enhanced seed oil. These assays can take many forms including, but not limited to, direct screening for the trait in a greenhouse or field trial or by screening for a surrogate trait. Such analyses can be directed to detecting changes in the chemical composition, biomass, physiological property, or morphology of the plant. Changes in chemical compositions such as nutritional composition of grain can be detected by analysis of the seed composition and content of protein, free amino acids, oil, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green or delayed senescence, stalk lodging, root lodging, plant health, bareness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates screening assays for corn traits using hybrid corn plants. The assays can be adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified by screening transgenic plants in the field under reduced amount of nitrogen supply as compared to control plants, where such plants provide the same or similar yield as compared to control plants.

Transgenic corn plants having increased yield are identified by screening using progenies of the transgenic plants over multiple locations for several years with plants grown under optimal production management practices and maximum weed and pest control or standard agronomic practices (SAP). Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, quinoa and sugar cane plants.

EXAMPLE 1

Corn Transformation

This example illustrates transformation methods in producing a transgenic corn plant cell, seed, and plant having altered phenotypes as shown in Tables 4-6, or an enhanced trait, for example, increased water use efficiency, increased nitrogen use efficiency, and increased yield as shown in Tables 7 and 8.

For *Agrobacterium*-mediated transformation of corn embryo cells corn plants were grown in the greenhouse and ears were harvested when the embryos were 1.5 to 2.0 mm in length. Ears were surface-sterilized by spraying or soaking the ears in 80% ethanol, followed by air drying. Immature embryos were isolated from individual kernels on surface-sterilized ears. Shortly after excision, immature maize embryos were inoculated with overnight grown *Agrobacterium* cells, and incubated at room temperature with *Agrobacterium* for 5-20 minutes. Inoculated immature embryos were then co-cultured with *Agrobacterium* for 1 to 3 days at 23° C. in the dark. Co-cultured embryos were transferred to selection media and cultured for approximately two weeks to allow embryogenic callus to develop. Embryogenic calli were transferred to culture medium containing glyphosate and subcultured at about two week intervals. Transformed plant cells were recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants individual transgenic calli resulting from transformation and selection were placed on media to initiate shoot and root development into plantlets. Plantlets were transferred to potting soil for initial growth in a growth chamber at 26° C. followed by a mist bench before transplanting to 5 inch pots where plants were grown to maturity. The regenerated plants were self-fertilized and seeds were harvested for use in one or more methods to select seeds, seedlings or progeny second generation transgenic plants (R2 plants) or hybrids, for example, by selecting transgenic plants exhibiting an enhanced trait as compared to a control plant.

The above process can be repeated to produce multiple events of transgenic corn plants from cells that were transformed with recombinant DNA from the genes identified in Table 1 or with recombinant DNA from Table 2 that is transcribed into a non-coding miRNA. Progeny transgenic plants and seeds of the transformed plants were screened for the presence and single copy of the inserted gene, and for increased water use efficiency, increased yield, increased nitrogen use efficiency, and altered phenotypes as shown in Tables 4-6. From each group of multiple events of transgenic plants with a specific recombinant DNA from Table 1 or Table 2, the event(s) that showed increased yield, increased water use efficiency, increased nitrogen use efficiency, and altered phenotypes was (were) identified.

EXAMPLE 2

Soybean Transformation

This example illustrates plant transformation in producing a transgenic soybean plant cell, seed, and plant having altered phenotypes, or an enhanced trait, for example, increased water use efficiency or drought tolerance and increased yield as shown in Tables 7 and 8.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA from the genes identified in Table 1 or recombinant DNA transcribed into a miRNA identified in Table 2. Progeny transgenic plants and seed of the transformed plant cells were screened for the presence and single copy of the inserted gene, and for increased water use efficiency and increased yield as shown in Tables 7 and 8.

EXAMPLE 3

Identification of Altered Phenotypes in Automated Greenhouse

This example illustrates screening and identification of transgenic plants for altered phenotypes in an automated greenhouse (AGH). The apparatus and the methods for automated phenotypic screening of plants are disclosed in US Patent publication No. US20110135161 (filed on Nov. 10, 2010), which is incorporated by reference herein in its entirety.

Screening and identification of transgenic corn plants for altered phenotypes.

Corn plants were tested in 3 screens in AGH under different conditions including non-stress, nitrogen deficit and water deficit stress conditions. All screens began with a non-stress condition during day 0-5 germination phase, after which the plants were grown for 22 days under screen specific conditions as shown in Table 3.

TABLE 3

Description of the 3 AGH screens for corn plants

| Screen | Description | Germination phase (5 days) | Screen specific phase (22 days) |
|---|---|---|---|
| Non-stress | well watered sufficient nitrogen | 55% VWC water | 55% VWC 8 mM nitrogen |
| Water deficit | limited watered sufficient nitrogen | 55% VWC water | 30% VWC 8 mM nitrogen |
| Nitrogen deficit | well watered low nitrogen | 55% VWC water | 55% VWC 2 mM nitrogen |

Water deficit is defined as a specific Volumetric Water Content (VWC) that is lower than the VWC of non-stress plant. For example, a non-stressed plant might be maintained at 55% VWC and the VWC for a water-deficit assay might be defined around 30% VWC as shown in Table 3. Data were collected using visible light and hyperspectral imaging as well as direct measurement of pot weight and amount of water and nutrient applied to individual plants on a daily basis.

Nitrogen deficit is defined in part as a specific mM concentration of nitrogen that is lower than the nitrogen concentration of non-stress plants. For example, a non-stress plant might be maintained at 8 mM nitrogen while the nitrogen concentration applied in a nitrogen-deficit assay might be maintained at a concentration of 2 mM.

Up to ten parameters were measured for each screen. The visible light color imaging based measurements are: biomass, canopy area and plant height. Biomass (Bmass) is defined as estimated shoot fresh weight (g) of the plant obtained from images acquired from multiple angles of view. Canopy Area (Cnop) is defined as area of leaf as seen in top-down image (mm$^2$). Plant Height (PlntH) refers to the distance from the top of the pot to the highest point of the plant derived from side image (mm). Anthocyanin score and area, chlorophyll concentration are hyperspectral imaging based parameters. Anthocyanin Score (AntS) is an estimate of anthocyanin in the leaf canopy obtained from a top-down hyperspectral image. Anthocyanin Area (AntA) is an estimate of anthocyanin in the stem obtained from a side-view hyperspectral image. Cholrophyll Concentration (ClrpC) is measurement of chlorophyll in the leaf canopy obtained from a top-down hyperspectral image, and it is measured in ppm units. Water Use Efficiency (WUE) is derived from the grams of plant biomass per liter of water added. Water Applied (WtrAp) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Tables 4-6 are summaries of transgenic corn plants comprising the disclosed recombinant DNA constructs with altered phenotypes under non stress, nitrogen deficit, and water deficit conditions, respectively.

The test results are represented by three numbers: the first number before letter "p" denotes number of events with an increase in the tested parameter at $p \leq 0.1$; the second number before letter "n" denotes number of events with an decrease in the tested parameter at $p \leq 0.1$; the third number before letter "t" denotes total number of transgenic events tested for a given parameter in a specific screen. The increase or decrease is measured in comparison to non-transgenic control plants. A "—" means that it has not been tested. For example, 2p1n5t indicates that 5 transgenic plant events were screened, of which 2 events showed increase and 1 showed decrease of the measured parameter.

TABLE 4

Summary of transgenic corn plants with altered phenotypes in AGH non-stress screens

| Gene_ID | AntA | AntS | Bmass | ClrpC | Cnop | PlntH | WUE | WtrAp |
|---|---|---|---|---|---|---|---|---|
| TRDX4M-1 | 0p0n5t | 0p1n5t | 0p2n5t | 1p0n5t | 0p1n5t | 0p1n5t | 0p2n5t | 0p1n5t |
| TRDX4M-1T | — | 0p0n5t | 0p1n5t | 0p0n5t | 0p1n5t | 0p1n5t | 0p1n5t | 0p0n5t |
| TRDX4M-4 | 0p0n5t | 0p1n5t | 0p5n5t | 0p0n5t | 0p3n5t | 0p3n5t | 0p2n5t | 0p3n5t |

TABLE 5

Summary of transgenic corn plants with altered phenotypes in AGH nitrogen-deficit screens

| Gene_ID | AntA | AntS | Bmass | ClrpC | Cnop | PlntH | WUE | WtrAp |
|---|---|---|---|---|---|---|---|---|
| TRDX4M-1 | 0p0n5t | 0p0n5t | 0p1n5t | 0p0n5t | 0p0n5t | 0p1n5t | 0p0n5t | 1p1n5t |
| TRDX4M-1T | — | 0p2n5t | 0p0n5t | 5p0n5t | 0p0n5t | 0p0n5t | 1p0n5t | 2p0n5t |
| TRDX4M-4 | 0p4n5t | 0p1n5t | 4p0n5t | 3p0n5t | 1p0n5t | 2p0n5t | 3p0n5t | 5p0n5t |

TABLE 6

Summary of transgenic corn plants with altered phenotypes in AGH water-deficit screens

| Gene_ID | AntA | AntS | Bmass | ClrpC | Cnop | PlntH | WUE | WtrAp |
|---|---|---|---|---|---|---|---|---|
| TRDX4M-1 | 0p1n5t | 1p0n5t | 0p1n5t | 2p0n5t | 0p1n5t | 1p0n5t | 0p0n5t | 0p1n5t |
| TRDX4M-1T | — | 0p1n5t | 0p1n5t | 2p0n5t | 0p0n5t | 0p2n5t | 0p0n5t | 0p3n5t |
| TRDX4M-4 | 0p0n5t | 0p0n5t | 1p0n5t | 2p0n5t | 1p0n5t | 0p1n5t | 1p0n5t | 0p3n5t |

EXAMPLE 4

Phenotypic Evaluation of Transgenic Plants for Increased Nitrogen Use Efficiency, Increased Water Use Efficiency and Increased Yield Corn field trials were conducted to identify genes that can improve nitrogen use efficiency (NUE) under nitrogen limiting conditions leading to increased yield performance as compared to non transgenic controls. For the Nitrogen field trial results shown in Tables 7 and 8, each field was planted under nitrogen limiting condition (60 lbs/acre) and corn ear weight or yield was compared to non transgenic control plants.

Corn field trials were conducted to identify genes that can improve water use efficiency (WUE) under water limiting conditions leading to increased yield performance as compared to non transgenic controls. The water use efficiency trials for results shown in Tables 7 and 8 were conducted under managed water limiting conditions, and the corn ear weight or yield was compared to non transgenic control plants.

Corn and soybean field trials were conducted to identify genes that can improve broad-acre yield (BAY) under standard agronomic practice. The broad-acre yield trials for results shown in Tables 7 and 8 were conducted under standard agronomic practice, and the corn or soybean yield was compared to non transgenic control plants.

Table 7 provides a list of genes for producing transgenic plants with increased nitrogen use efficiency (NUE), increased water use efficiency (WUE), and increased broad-acre yield (BAY) as compared to a control plant. Polynucleotide sequences in constructs with at least one event showing significant yield or ear weight increase across multiple locations at $p \leq 0.2$ are included. The genes were expressed with constitutive promoters unless noted otherwise under "Specific Expression Pattern". Promoter of specific expression pattern was chosen over constitutive promoter, based on the understanding of the gene function, or based on the observed lack of significant yield increase when the gene was expressed with constitutive promoter. The elements of Table 7 are described by reference to:

"Crop" which refers to the crop in trial, which is either corn or soybean;

"Condition" which refers to the type of field trial, which is BAY for broad acre yield trial under standard agronomic practice (SAP), WUE for water use efficiency trial, and NUE for nitrogen use efficiency trial;

"Gene ID" which refers to the gene identifier as defined in Table 1;

"Yield results" which refers to the recombinant DNA in a construct with at least one event showing significant yield increase at $p \leq 0.2$ across locations. The first number refers to the number of events with significant yield or ear weight increase, whereas the second number refers to the total number of events tested for each recombinant DNA in the construct.

TABLE 7

Recombinant DNA with protein-coding genes for increased nitrogen use efficiency, increased water use efficiency and increased yield

| Crop | Condition | Gene ID | Yield Results |
|---|---|---|---|
| Corn | BAY | TRDX4M-1 | 1/20 |
| Soybean | BAY | TRDX4M-2 | 3/24 |
| Soybean | BAY | TRDX4M-3 | 4/14 |
| Corn | BAY | TRDX4M-4 | 1/22 |
| Soybean | BAY | TRDX4M-5 | 4/16 |

Table 8 provides a list of suppression target genes and miRNA construct elements provided as recombinant DNA for production of transgenic corn or soybean plants with increased nitrogen use efficiency, increased water use efficiency and increased yield. The elements of Table 8 are described by reference to:

"Crop" which refers to the crop in trial, which is either corn or soy;

"Condition" which refers to the type of field trial, which is BAY for broad acre yield trial under standard agronomic practice, WUE for water use efficiency trial, and NUE for nitrogen use efficiency trial;

"Target Gene ID" which refers to the suppression target gene identifier as defined in Table 2;

"Engineered miRNA precursor SEQ ID NO." which identifies a nucleotide sequence of the miRNA construct;

"Yield results" which refers to the recombinant DNA in a construct with at least one event showing significant yield increase at p≤0.2 across locations. The first number refers to the number of events with significant yield or ear weight increase, whereas the second number refers to the total number of events tested for each sequence in the construct.

TABLE 8 miRNA Recombinant DNA constructs suppressing targeted genes for increased nitrogen use efficiency, increased water use efficiency and increased yield

| Crop | Condition | Target Gene ID | Engineered miRNA precursor SEQ ID NO. | Yield Results |
|---|---|---|---|---|
| corn | WUE | TRDX4M-1T | 13 | 1/5 |

EXAMPLE 5

Homolog Identification

This example illustrates the identification of homologs of proteins encoded by the DNA identified in Table 1 which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided in Table 1 using NCBI "blastp" program with E-value cutoff of 1e−8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp" program with E-value cutoff of 1e−4. Up to 1000 top hits were kept. A BLAST searchable database was constructed based on these hits, and is referred to as "SubDB". SubDB is queried with each sequence in the Hit List using NCBI "blastp" program with E-value cutoff of 1e−8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs with at least 95% identity over 95% of the length of the polypeptide sequences provided in Table 1 are reported below in Tables 9 and 10.

Table 9 provides a list of homolog genes, of which the elements are described by reference to:

"PEP SEQ ID NO." which identifies an amino acid sequence.

"Homolog ID" which refers to an alphanumeric identifier, the numeric part of which is the NCBI Genbank GI number.

"Gene Name and Description" which is a common name and functional description of the gene.

TABLE 9

Homolog genes information

| PEP SEQ ID NO. | Homolog ID | Gene Name and Description |
|---|---|---|
| 15 | gi_30695456 | gi|30695456|ref|NP_564624.2| TCP3; transcription factor [Arabidopsis thaliana] gi|75192198|sp|Q9MAH8|TCP3_ARATH RecName: Full = Transcription factor TCP3 gi|7769872|gb|AAF69550.1|AC008007_25 F12M16.13 [Arabidopsis thaliana] gi|20466424|gb|AAM20529.1| putative flower development protein cycloidea [Arabidopsis thaliana] gi|23198116|gb|AAN15585.1| putative flower development protein cycloidea [Arabidopsis thaliana] |
| 16 | gi_21593425 | gi|21593425|gb|AAM65392.1| NAM protein, putative [Arabidopsis thaliana] |
| 17 | gi_293335733 | gi|293335733|ref|NP_001169344.1| hypothetical protein LOC100383211 [Zea mays] gi|224028835|gb|ACN33493.1| unknown [Zea mays] |

Table 10 describes the correspondence between the protein-coding genes in Table 1, suppression target genes in Table 2, and their homologs, and the level of protein sequence alignment between the gene and its homolog.

TABLE 10

Correspondence of Genes and Homologs

| Gene ID | Homolog ID | Percent Gene Coverage | Percent Homolog Coverage | Percent Identity |
|---|---|---|---|---|
| TRDX4M-1 | gi_30695456 | 100 | 95 | 100 |
| TRDX4M-4 | gi_21593425 | 100 | 100 | 98 |
| TRDX4M-1T | gi_293335733 | 100 | 100 | 98 |

EXAMPLE 6

Use of Suppression Methods to Suppress Expression of Target Genes

This example illustrates monocot and dicot plant transformation with recombinant DNA constructs that are useful for stable integration into plant chromosomes in the nuclei of plant cells to provide transgenic plants having enhanced traits by suppression of the expression of target genes.

Various recombinant DNA constructs for use in suppressing the expression of a target gene in transgenic plants are constructed based on the nucleotide sequence of the gene encoding the protein that has an amino acid sequence of SEQ ID NO. 12, where the DNA constructs are designed to express (a) a miRNA that targets the gene for suppression, (b) an RNA that is a messenger RNA for a target protein and has a synthetic miRNA recognition site that results in down modulation of the target protein, (c) an RNA that forms a dsRNA and that is processed into siRNAs that effect down regulation of the target protein, (d) a ssRNA that forms a transacting siRNA which results in the production of siRNAs that effect down regulation of the target protein.

Each of the various types of recombinant DNA constructs is used in transformation of a corn cell using the vector and method of Examples 1 and 2 to produce multiple events of transgenic corn cell. Such events are regenerated into transgenic corn plants and are screened to confirm the presence of the recombinant DNA and its expression of RNA for suppression of the target protein. The population of transgenic plants from multiple transgenic events are also screened to identify the transgenic plants that exhibit altered phenotype or enhanced trait.

We claim:

1. A recombinant DNA construct comprising a heterologous promoter functional in a plant cell and operably linked to:
   a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to SEQ ID NO:5; or
   b) a polynucleotide that encodes a polypeptide having an amino acid sequence with at least 95%, at least 96%, at least 97%, at least 98%, at least 99% identity, or 100% identity to a sequence selected from the group consisting of SEQ ID NO:10.

2. A plant comprising a recombinant DNA construct comprising a heterologous promoter functional in a plant cell and operably linked to:
   a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to SEQ ID NO:5; or
   b) a polynucleotide that encodes a polypeptide having an amino acid sequence with at least 95%, at least 96%, at least 97%, at least 98%, at least 99% identity, or 100% identity to SEQ ID NO:10.

3. The plant of claim 2, wherein said plant has an altered phenotype or an enhanced trait as compared to a control plant.

4. The plant of claim 2, wherein said plant is a progeny, a propagule, or a field crop.

5. The plant of claim 2, wherein said plant is a corn, soybean, cotton, canola, rice, barley, oat, wheat, turf grass, alfalfa, sugar beet, sunflower, quinoa or sugar cane field crop.

6. The plant of claim 2, wherein said plant is a cell, pollen, ovule, flower, embryo, leaf, root, stem, shoot, meristem, grain or seed propagule.

7. The plant of claim 3, wherein said enhanced trait is increased yield, increased nitrogen use efficiency, or increased water use efficiency as compared to a control plant.

8. The plant of claim 3, wherein said phenotype is anthocyanin content, biomass, canopy area, chlorophyll content, plant height, water applied, or water use efficiency.

9. A method for increasing yield, increasing nitrogen use efficiency, or increasing water use efficiency in a plant comprising producing a plant comprising a recombinant DNA construct comprising a heterologous promoter functional in a plant cell and operably linked to:
   a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to SEQ ID NO:5; or
   b) a polynucleotide that encodes a polypeptide having an amino acid sequence with at least 95%, at least 96%, at least 97%, at least 98%, at least 99% identity, or 100% identity to SEQ ID NO:10.

10. The method of claim 9 wherein said plant is produced by transforming a plant cell or tissue with said recombinant DNA construct and regenerating a plant from said cell or tissue containing said recombinant DNA construct.

11. The method of claim 9 comprising producing said plant by crossing said plant through breeding with:
    a) itself;
    b) a second plant from the same plant line;
    c) a wild type plant; or
    d) a second plant from a different line of plants
    to produce a seed, growing said seed to produce a plurality of progeny plants; and selecting a progeny plant with increased yield, increased nitrogen use efficiency, or increased water use efficiency as compared to a control plant.

12. The recombinant DNA construct of claim 1, wherein the polynucleotide comprises a nucleotide sequence with at least 95% identity to SEQ ID NO:5.

13. The recombinant DNA construct of claim 1, wherein the polynucleotide comprises the nucleotide sequence of SEQ ID NO:5.

14. The recombinant DNA construct of claim 1, wherein the polynucleotide encodes a polypeptide having at least 95% identity to SEQ ID NO:10.

15. The recombinant DNA construct of claim 1, wherein the polynucleotide encodes a polypeptide comprising the sequence of SEQ ID NO:10.

* * * * *

SEQUENCE LISTING

<160> NUMBER OF SEQ ID NOS: 21

<210> SEQ ID NO 1
<211> LENGTH: 1122
<212> TYPE: DNA
<213> ORGANISM: Arabidopsis thaliana

<400> SEQUENCE: 1

```
atgagacacc accaatcagc gacggagaac ggtggtggtt gcggcgagat tgtggaggta      60
caaggaggtc acattgttcg gtcaacagga agaaaagaca gacatagtaa agtatgtaca     120
gcgaaaggac cacgtgaccg gcgcgtgaga ctctcagctc cgacggcgat tcaattctac     180
gatgttcaag atagacttgg ttttgatcga ccaagtaaag ctgttgattg gcttattact     240
aaagctaaat ccgccattga tgatcttgct cagcttcctc cttggaaccc cgccgatact     300
cttcgtcaac acgccgccgc tgctgctaac gctaaaccca gaaaaaccaa aactttaatt     360
tctccgccac cgccacaacc ggaagaaaca gagcatcatc gaatcggaga agaagaagat     420
aacgaatcga gttttcttcc ggcgtcaatg gattctgatt cgatagctga cactataaag     480
tcgttttttc cggtagcttc aacgcaacag agctatcatc atcagccacc gtcacgaggc     540
aatacacaga accaagatct tcttcgtctc tcgcttcaat ctttccaaaa tggtccacct     600
tttcctaatc aaacagaacc tgctctgttc tccggccaga gcaataatca gttagcgttt     660
gactcatcga cggcaagctg ggaacagagt catcagtcac cggaatttgg aaagatacag     720
agactagtgt catggaacaa cgtcggagca gctgaatccg ccggaagtac cggaggattt     780
gtgtttgctt ctccgtcgtc gttgcatcca gtttatagcc aaagtcagct tttatcacag     840
aggggtcccc ttcagtccat taacacacct atgattcgtg cttggtttga tcctcaccat     900
catcatcatc atcatcagca gtccatgacc actgacgatc tccaccatca tcatccctac     960
catatccctc ccgggattca ccaatctgct attccaggca ttgcatttgc ttcaagtggt    1020
gaattctccg gttttcgtat accagcacgg tttcaaggcg aacaagagga gcacggcggc    1080
gacaacaagc cgtcctctgc ttcatccgat tctcgccatt ag                       1122
```

<210> SEQ ID NO 2
<211> LENGTH: 630

<212> TYPE: DNA
<213> ORGANISM: Artificial
<220> FEATURE:
<223> OTHER INFORMATION: variant of Arabidopsis B-box32 gene, with 157-174aa deletion

<400> SEQUENCE: 2

```
atggtgagct tttgcgagct tgtggtgcc gaagctgatc tccattgtgc cgcggactct      60
gccttcctct gccgttcttg tgacgctaag ttccatgcct caaattttct cttcgctcgt    120
catttccggc gtgtcatctg cccaaattgc aaatctctta ctcaaaattt cgtttctggt    180
cctcttcttc cttggcctcc acgaacaaca tgttgttcag aatcgtcgtc ttcttcttgc    240
tgctcgtctc ttgactgtgt ctcaagctcc gagctatcgt caacgacgcg tgacgtaaac    300
agagcgcgag ggagggaaaa cagagtgaat gccaaggccg ttgcggttac ggtggcggat    360
ggcatttttg taaattggtg tggtaagtta ggactaaaca gggatttaac aaacgctgtc    420
gtttcatatg cgtctttggc tttggctgtg gagacgaggc caagagcgac gacgacgtgg    480
cagaatttaa agaaagtaga gatgtgact ggagtttcag ctgggatgat cgagcggtt     540
gaaagcaaat tggcgcgtgc aatgacgcag cagcttagac ggtggcgcgt ggattcggag    600
gaaggatggg ctgaaaacga caacgtttga                                     630
```

<210> SEQ ID NO 3
<211> LENGTH: 138
<212> TYPE: DNA
<213> ORGANISM: Artificial
<220> FEATURE:
<223> OTHER INFORMATION: Variant of Arabidopsis ERF/AP2 (ethylene response factor) subfamily B-3 transcription factor, with 46aa-Cterminus truncation

<400> SEQUENCE: 3

```
atggatcaag gaggtcgtag cagtggtagt ggaggaggag gagccgagca agggaagtac      60
cgtggagtaa ggagacgacc ttggggtaaa tacgccgcgg aaataagaga ttcgaggaag    120
cacggagagc gtgtgtga                                                   138
```

<210> SEQ ID NO 4
<211> LENGTH: 972
<212> TYPE: DNA
<213> ORGANISM: Arabidopsis thaliana

<400> SEQUENCE: 4

```
atggaaaaca tggggattc gagcataggg ccgggccatc cgcatctccc tcccgggttt      60
cggtttcacc cgactgatga ggaactagta gttcattacc tcaagaagaa agcagattct    120
gttccacttc cagtctcaat catcgcagag attgatcttt acaagtttga tccttgggag    180
cttccaagca aggcgagttt tggagagcac gagtggtact tctttagtcc tcgggatcgg    240
aagtatccaa atggggttag gccaaaccgg gcagcaactt ccggttattg gaaagcaacg    300
ggaaccgata aaccgatatt tacgtgcaat agtcacaagg ttggtgtcaa gaaagcgctt    360
gttttttacg gtggaaagcc tcctaaaggg ataaaaacag attggatcat gcatgaatat    420
cgcctcactg atggtaacct tagcactgcg gctaagccgc ctgacttaac cacgacaagg    480
aaaaactcac tacggctaga cgattgggtt ctatgtagga tctataagaa gaatagttca    540
caaagaccaa caatggagag agtattactt agagaggatc taatggaagg catgctctca    600
aaatcatctg ctaattcttc ttctacatca gtactagaca caacgacaa caataataac     660
aataacgaag aacacttttt cgacggtatg gtcgtttctt cagacaaacg ttccttgtgt    720
```

| | |
|---|---|
| ggtcaatacc gaatgggcca cgaggcctca ggatcatctt cattcggatc tttcttatcg | 780 |
| agcaagaggt ttcatcatac aggtgatctc aacaatgata actacaatgt ctcttttgtt | 840 |
| tcgatgctta gtgagattcc tcagagttcg gggtttcatg caaatggtgt tatggatacg | 900 |
| acgtcgtctc tagctgatca tggggtttta agacaggcgt tcagcttcc taacatgaac | 960 |
| tggcactcat aa | 972 |

<210> SEQ ID NO 5
<211> LENGTH: 1671
<212> TYPE: DNA
<213> ORGANISM: Glycine max

<400> SEQUENCE: 5

| | |
|---|---|
| atggacatgg acgtggaaga agcttctgca cctaaagaga gaaagcccgt tttggtgatc | 60 |
| ttggtgggcg ctccagggag cgggaagtcc accttctgcg aagaagttat gggttcctct | 120 |
| actcgccctt gggttcgcgt ttgccaggac actattggaa atggtaaagc aggaaataaa | 180 |
| gctcagtgcc taagcagtgc aactagagca ttgaaggatg gaagagtgt atttattgat | 240 |
| aggtgcaatc ttgacagaga acagcgttca gaatttataa agcttggtga tggaccccaa | 300 |
| atagatgtcc atgcagttgt acttgatctt cctgctaagc tttgtatttc tcgatcagtc | 360 |
| aaacgaactg gcatgaagg aaatttgcag ggtggaaaag ctgctgcagt tgtgaataga | 420 |
| atgcttcaac ataaagagct tcccaaatta gtgaaggct ttagccggat aacattttgt | 480 |
| cagaatgaaa gtgatgtaaa aatgctctt aacacataca gcacacttgg gccactggat | 540 |
| agtcttcaat atggctgctt tggccagaag aatcctgatt ccaaaattca gttggtata | 600 |
| atgaagttcc ttaaaagagc agaggtccca gttgctgctg catctagaga gagtggcatt | 660 |
| gaagacccta cttcccagac tccgggtaaa ataactcct gctgcaaaga taagcaaaca | 720 |
| ttttcctcaa ttcctgataa tgacaactca gagacgaagg aagtagaaaa ccaagcagtt | 780 |
| ggctctgttg gttcccatgc caatcaagtt tctctggatg atattcccac tctggcattt | 840 |
| ccatctattt caacatctga ttttcaattc aaccatgaga aggcagctga tattattgtt | 900 |
| gagaaggttg cagagttctc aaataagttt aggaatgcca gacttgttct tgttgacttg | 960 |
| tctcataaat caaagattct gtccttagtt aaggctaaaa ttgcaggaaa aaacattgat | 1020 |
| gcccaaaagt tctttaccca tgttggggac attactcatc tttattccag gggaggtttg | 1080 |
| cgatgtaatg tcattgctaa cgctgccaac tggaggttaa atcctggagg tggaggtgta | 1140 |
| aatgcagcaa ttttaatgc tgcaggtcct gaactggagt ctgcaacaaa agaaaaagta | 1200 |
| caatctcttt ctccagggaa tgctgctgtt gttcctctac cttcatcttc tcctttgttc | 1260 |
| accagagagg gtgtaaccca tgtaatacat gttgttggac taatatgaa cccacaaaga | 1320 |
| ccaaattgtc taaataatga ttataataaa ggctgcaaaa ttctccaaga tgcttatact | 1380 |
| tcacttttg aaggctttgc atctattgtg acaaacctga catggcaacc agttggaaaa | 1440 |
| actgaaaacc ttgaaaggaa gtctttaatg ttgcaggttc agtctaattg ttccagaaat | 1500 |
| tatttcacaa aaatagatca aaagagtaaa agagatgttg atcatggatc aacaaaaagc | 1560 |
| aagaaataca aggggactca ggatggttct ggattgacct ttactgattc tagggatgaa | 1620 |
| aatgttgatt cagagcatag aagaactgag aggagcatga gtaaggcatg a | 1671 |

<210> SEQ ID NO 6
<211> LENGTH: 373
<212> TYPE: PRT

<213> ORGANISM: Arabidopsis thaliana

<400> SEQUENCE: 6

Met Arg His His Gln Ser Ala Thr Glu Asn Gly Gly Gly Cys Gly Glu
1               5                   10                  15

Ile Val Glu Val Gln Gly Gly His Ile Val Arg Ser Thr Gly Arg Lys
            20                  25                  30

Asp Arg His Ser Lys Val Cys Thr Ala Lys Gly Pro Arg Asp Arg Arg
        35                  40                  45

Val Arg Leu Ser Ala Pro Thr Ala Ile Gln Phe Tyr Asp Val Gln Asp
    50                  55                  60

Arg Leu Gly Phe Asp Arg Pro Ser Lys Ala Val Asp Trp Leu Ile Thr
65                  70                  75                  80

Lys Ala Lys Ser Ala Ile Asp Asp Leu Ala Gln Leu Pro Pro Trp Asn
                85                  90                  95

Pro Ala Asp Thr Leu Arg Gln His Ala Ala Ala Ala Asn Ala Lys
            100                 105                 110

Pro Arg Lys Thr Lys Thr Leu Ile Ser Pro Pro Pro Gln Pro Glu
        115                 120                 125

Glu Thr Glu His His Arg Ile Gly Glu Glu Asp Asn Glu Ser Ser
130                 135                 140

Phe Leu Pro Ala Ser Met Asp Ser Asp Ser Ile Ala Asp Thr Ile Lys
145                 150                 155                 160

Ser Phe Phe Pro Val Ala Ser Thr Gln Gln Ser Tyr His His Gln Pro
                165                 170                 175

Pro Ser Arg Gly Asn Thr Gln Asn Gln Asp Leu Leu Arg Leu Ser Leu
            180                 185                 190

Gln Ser Phe Gln Asn Gly Pro Pro Phe Pro Asn Gln Thr Glu Pro Ala
        195                 200                 205

Leu Phe Ser Gly Gln Ser Asn Asn Gln Leu Ala Phe Asp Ser Ser Thr
    210                 215                 220

Ala Ser Trp Glu Gln Ser His Gln Ser Pro Glu Phe Gly Lys Ile Gln
225                 230                 235                 240

Arg Leu Val Ser Trp Asn Asn Val Gly Ala Ala Glu Ser Ala Gly Ser
                245                 250                 255

Thr Gly Gly Phe Val Phe Ala Ser Pro Ser Ser Leu His Pro Val Tyr
            260                 265                 270

Ser Gln Ser Gln Leu Leu Ser Gln Arg Gly Pro Leu Gln Ser Ile Asn
        275                 280                 285

Thr Pro Met Ile Arg Ala Trp Phe Asp Pro His His His His
    290                 295                 300

His Gln Gln Ser Met Thr Thr Asp Asp Leu His His His His Pro Tyr
305                 310                 315                 320

His Ile Pro Pro Gly Ile His Gln Ser Ala Ile Pro Gly Ile Ala Phe
                325                 330                 335

Ala Ser Ser Gly Glu Phe Ser Gly Phe Arg Ile Pro Ala Arg Phe Gln
            340                 345                 350

Gly Glu Gln Glu Glu His Gly Gly Asp Asn Lys Pro Ser Ser Ala Ser
        355                 360                 365

Ser Asp Ser Arg His
    370

<210> SEQ ID NO 7
<211> LENGTH: 209

```
<212> TYPE: PRT
<213> ORGANISM: Artificial
<220> FEATURE:
<223> OTHER INFORMATION: variant of Arabidopsis B-box32 gene, with 157-
      174aa deletion

<400> SEQUENCE: 7

Met Val Ser Phe Cys Glu Leu Cys Gly Ala Glu Ala Asp Leu His Cys
1               5                   10                  15

Ala Ala Asp Ser Ala Phe Leu Cys Arg Ser Cys Asp Ala Lys Phe His
            20                  25                  30

Ala Ser Asn Phe Leu Phe Ala Arg His Phe Arg Arg Val Ile Cys Pro
        35                  40                  45

Asn Cys Lys Ser Leu Thr Gln Asn Phe Val Ser Gly Pro Leu Leu Pro
50                  55                  60

Trp Pro Pro Arg Thr Thr Cys Cys Ser Glu Ser Ser Ser Ser Ser Cys
65                  70                  75                  80

Cys Ser Ser Leu Asp Cys Val Ser Ser Glu Leu Ser Ser Thr Thr
                85                  90                  95

Arg Asp Val Asn Arg Ala Arg Gly Arg Glu Asn Arg Val Asn Ala Lys
                100                 105                 110

Ala Val Ala Val Thr Val Ala Asp Gly Ile Phe Val Asn Trp Cys Gly
            115                 120                 125

Lys Leu Gly Leu Asn Arg Asp Leu Thr Asn Ala Val Val Ser Tyr Ala
        130                 135                 140

Ser Leu Ala Leu Ala Val Glu Thr Arg Pro Arg Ala Thr Thr Thr Trp
145                 150                 155                 160

Gln Asn Leu Lys Lys Val Glu Asp Val Thr Gly Val Ser Ala Gly Met
                165                 170                 175

Ile Arg Ala Val Glu Ser Lys Leu Ala Arg Ala Met Thr Gln Gln Leu
            180                 185                 190

Arg Arg Trp Arg Val Asp Ser Glu Gly Trp Ala Glu Asn Asp Asn
        195                 200                 205

Val

<210> SEQ ID NO 8
<211> LENGTH: 45
<212> TYPE: PRT
<213> ORGANISM: Artificial
<220> FEATURE:
<223> OTHER INFORMATION: Variant of Arabidopsis ERF/AP2 (ethylene
      response factor) subfamily B-3 transcription factor, with 46aa-
      Cterminus truncation

<400> SEQUENCE: 8

Met Asp Gln Gly Gly Arg Ser Ser Gly Ser Gly Gly Gly Ala Glu
1               5                   10                  15

Gln Gly Lys Tyr Arg Gly Val Arg Arg Arg Pro Trp Gly Lys Tyr Ala
            20                  25                  30

Ala Glu Ile Arg Asp Ser Arg Lys His Gly Glu Arg Val
        35                  40                  45

<210> SEQ ID NO 9
<211> LENGTH: 323
<212> TYPE: PRT
<213> ORGANISM: Arabidopsis thaliana

<400> SEQUENCE: 9

Met Glu Asn Met Gly Asp Ser Ser Ile Gly Pro Gly His Pro His Leu
```

```
  1               5                  10                  15
Pro Pro Gly Phe Arg Phe His Pro Thr Asp Glu Glu Leu Val Val His
             20                  25                  30

Tyr Leu Lys Lys Lys Ala Asp Ser Val Pro Leu Pro Val Ser Ile Ile
             35                  40                  45

Ala Glu Ile Asp Leu Tyr Lys Phe Asp Pro Trp Glu Leu Pro Ser Lys
 50                  55                  60

Ala Ser Phe Gly Glu His Glu Trp Tyr Phe Phe Ser Pro Arg Asp Arg
 65                  70                  75                  80

Lys Tyr Pro Asn Gly Val Arg Pro Asn Arg Ala Ala Thr Ser Gly Tyr
                 85                  90                  95

Trp Lys Ala Thr Gly Thr Asp Lys Pro Ile Phe Thr Cys Asn Ser His
                100                 105                 110

Lys Val Gly Val Lys Lys Ala Leu Val Phe Tyr Gly Gly Lys Pro Pro
                115                 120                 125

Lys Gly Ile Lys Thr Asp Trp Ile Met His Glu Tyr Arg Leu Thr Asp
            130                 135                 140

Gly Asn Leu Ser Thr Ala Ala Lys Pro Pro Asp Leu Thr Thr Thr Arg
145                 150                 155                 160

Lys Asn Ser Leu Arg Leu Asp Asp Trp Val Leu Cys Arg Ile Tyr Lys
                165                 170                 175

Lys Asn Ser Ser Gln Arg Pro Thr Met Glu Arg Val Leu Leu Arg Glu
                180                 185                 190

Asp Leu Met Glu Gly Met Leu Ser Lys Ser Ser Ala Asn Ser Ser Ser
            195                 200                 205

Thr Ser Val Leu Asp Asn Asn Asp Asn Asn Asn Asn Asn Asn Glu Glu
210                 215                 220

His Phe Phe Asp Gly Met Val Val Ser Asp Lys Arg Ser Leu Cys
225                 230                 235                 240

Gly Gln Tyr Arg Met Gly His Glu Ala Ser Gly Ser Ser Phe Gly
                245                 250                 255

Ser Phe Leu Ser Ser Lys Arg Phe His His Thr Gly Asp Leu Asn Asn
                260                 265                 270

Asp Asn Tyr Asn Val Ser Phe Val Ser Met Leu Ser Glu Ile Pro Gln
            275                 280                 285

Ser Ser Gly Phe His Ala Asn Gly Val Met Asp Thr Thr Ser Ser Leu
            290                 295                 300

Ala Asp His Gly Val Leu Arg Gln Ala Phe Gln Leu Pro Asn Met Asn
305                 310                 315                 320

Trp His Ser

<210> SEQ ID NO 10
<211> LENGTH: 556
<212> TYPE: PRT
<213> ORGANISM: Glycine max

<400> SEQUENCE: 10

Met Asp Met Asp Val Glu Glu Ala Ser Ala Pro Lys Glu Arg Lys Pro
  1               5                  10                  15

Val Leu Val Ile Leu Val Gly Ala Pro Gly Ser Gly Lys Ser Thr Phe
                 20                  25                  30

Cys Glu Glu Val Met Gly Ser Ser Thr Arg Pro Trp Val Arg Val Cys
             35                  40                  45

Gln Asp Thr Ile Gly Asn Gly Lys Ala Gly Asn Lys Ala Gln Cys Leu
```

```
            50                  55                  60
Ser Ser Ala Thr Arg Ala Leu Lys Asp Gly Lys Ser Val Phe Ile Asp
65                  70                  75                  80

Arg Cys Asn Leu Asp Arg Glu Gln Arg Ser Glu Phe Ile Lys Leu Gly
                85                  90                  95

Asp Gly Pro Gln Ile Asp Val His Ala Val Val Leu Asp Leu Pro Ala
            100                 105                 110

Lys Leu Cys Ile Ser Arg Ser Val Lys Arg Thr Gly His Glu Gly Asn
        115                 120                 125

Leu Gln Gly Gly Lys Ala Ala Val Val Asn Arg Met Leu Gln His
    130                 135                 140

Lys Glu Leu Pro Lys Leu Ser Glu Gly Phe Ser Arg Ile Thr Phe Cys
145                 150                 155                 160

Gln Asn Glu Ser Asp Val Lys Asn Ala Leu Asn Thr Tyr Ser Thr Leu
                165                 170                 175

Gly Pro Leu Asp Ser Leu Gln Tyr Gly Cys Phe Gly Gln Lys Asn Pro
            180                 185                 190

Asp Ser Lys Ile Gln Val Gly Ile Met Lys Phe Leu Lys Arg Ala Glu
        195                 200                 205

Val Pro Val Ala Ala Ala Ser Arg Glu Ser Gly Ile Glu Asp Pro Thr
    210                 215                 220

Ser Gln Thr Pro Gly Lys Asn Asn Ser Cys Cys Lys Asp Lys Gln Thr
225                 230                 235                 240

Phe Ser Ser Ile Pro Asp Asn Asp Asn Ser Glu Thr Lys Glu Val Glu
                245                 250                 255

Asn Gln Ala Val Gly Ser Val Gly Ser His Ala Asn Gln Val Ser Leu
            260                 265                 270

Asp Asp Ile Pro Thr Leu Ala Phe Pro Ser Ile Ser Thr Ser Asp Phe
        275                 280                 285

Gln Phe Asn His Glu Lys Ala Ala Asp Ile Ile Val Glu Lys Val Ala
    290                 295                 300

Glu Phe Ser Asn Lys Phe Arg Asn Ala Arg Leu Val Leu Val Asp Leu
305                 310                 315                 320

Ser His Lys Ser Lys Ile Leu Ser Leu Val Lys Ala Lys Ile Ala Gly
                325                 330                 335

Lys Asn Ile Asp Ala Gln Lys Phe Phe Thr His Val Gly Asp Ile Thr
            340                 345                 350

His Leu Tyr Ser Arg Gly Gly Leu Arg Cys Asn Val Ile Ala Asn Ala
        355                 360                 365

Ala Asn Trp Arg Leu Asn Pro Gly Gly Gly Val Asn Ala Ala Ile
    370                 375                 380

Phe Asn Ala Ala Gly Pro Glu Leu Glu Ser Ala Thr Lys Glu Lys Val
385                 390                 395                 400

Gln Ser Leu Ser Pro Gly Asn Ala Ala Val Pro Leu Pro Ser Ser
                405                 410                 415

Ser Pro Leu Phe Thr Arg Glu Gly Val Thr His Val Ile His Val Val
            420                 425                 430

Gly Pro Asn Met Asn Pro Gln Arg Pro Asn Cys Leu Asn Asn Asp Tyr
        435                 440                 445

Asn Lys Gly Cys Lys Ile Leu Gln Asp Ala Tyr Thr Ser Leu Phe Glu
    450                 455                 460

Gly Phe Ala Ser Ile Val Thr Asn Leu Thr Trp Gln Pro Val Gly Lys
465                 470                 475                 480
```

```
Thr Glu Asn Leu Glu Arg Lys Ser Leu Met Leu Gln Val Gln Ser Asn
                485                 490                 495

Cys Ser Arg Asn Tyr Phe Thr Lys Ile Asp Gln Lys Ser Lys Arg Asp
            500                 505                 510

Val Asp His Gly Ser Thr Lys Ser Lys Lys Tyr Lys Gly Thr Gln Asp
        515                 520                 525

Gly Ser Gly Leu Thr Phe Thr Asp Ser Arg Asp Glu Asn Val Asp Ser
    530                 535                 540

Glu His Arg Arg Thr Glu Arg Ser Met Ser Lys Ala
545                 550                 555

<210> SEQ ID NO 11
<211> LENGTH: 1977
<212> TYPE: DNA
<213> ORGANISM: Zea mays

<400> SEQUENCE: 11
atgcaaggac agaggaattc tatggagcat tttgctgatg tctttggatt cgacgttgca    60
tcgagttcag caaccctgt gatggatcag cagtcatatt ggaataatgt tcttggatca   120
gtagaatcac ataatcttca aggttatcag atggctcaca gtgatgccgc catgccatat   180
gggaatgaac cacagcaaga tggtacattt cttggtttct gggaatcagg cgaagcaagt   240
gcaagtggca gctctaacaa tgccaaaaca gagcatctta atattggcgg tggtggtgga   300
ctgaggattg gtgaaagccg actggtagct gacaatggca tttctctgga tgtggatatc   360
aaccttaacg ccaacgttaa cgatctttgt ggtcaaagtt caaatgttaa ctgtgcctct   420
caaggtcctg agcagtattg tggcagtgat cgtaatgcta taattctca gccgactgac    480 ctgggattac acccattcag gacattccta ctagatgcac agcaagcaga atcttttact   540
ttgaatccta gtgaaaaccc tttgggtgat ttttcatcaa tgcaagaaag cattgaccaa   600
agaccaggtg gttccctgga tggtcgccgg ctagcgtgca agagaaaaaa tattgaagga   660
gccaatggcc agagttcagc aggtgctagt acaagttttc cccacaggaa cgataatgca   720
ttccataaca ttgcttcttc aagttacaat cctgcaccta tcagaaattc atcctctccc   780
aagtgtttgc cagttccaag ttctattgaa gatcaactcc cacggtatgg aactaatgta   840
gggctctcag ccggtactta tgaccttcat ggagggggtca acaatgctgt gaattcacag   900
agaagtttcc gagcaagaac taccacatct caacaggttg ctccctgtag tgtatggccc   960
tcttcaaatg ctatcagact ttctaattca tggaatcacc agccacctca tttccaaagt  1020
gcatttgatg atccccagga ggttattcct gtggtcagca gcctcaactt gcaataccaa  1080
catccaatga atgttcctgg tgtgccacag gctgctaacc gtttcactga ccatggagct  1140
tcatcatcga gagctgggag tttggagaac agaattattg gtagtgaaga ggttcctagg  1200
aggtatgccg cgcctaccaa ctactctgat ttagttcccc cacctgcagt agacctgaga  1260
cgtttggtgc cagaaccatt taattggagt tctgatgtcc gaggcactgc aatatcagga  1320
agtattattc ctcctgtatc aagaactaat aacagttcaa cagttaatcc accagcagga  1380
ttcaatcacc aaaacctcac cagacgccat cctcgaaatt tatcagagga gattggtcgt  1440
ctatctggag cactccgcgg ccatcaaccc ccacgcttaa ggtcagggtt tctgttggag  1500
cgtcagggcg atggtgtttg gggcgttcct ttatcaacaa ggggtagaga aggaagaagg  1560
ttaatggaga ttcggaatgc acttgaaatg attcaaaggg gggaaaatgt aaggctcgag  1620
tctatcttct atggcggcct cgacattcat gacagacaca gggacatgcg ccttgacatt  1680
```

```
gacaatatgt cctatgagga actattagca cttgaggaaa ggatcggaaa tgttagcact      1740
ggcctcagcg aggaagctgt gataaggttg ctcaaacaaa ggaaattttc atcgtggaca      1800
ctaaaagcat ctttggaccc tgaaccatgc tgtatctgcc aggaggagta cgctgatgga      1860
gacgacctcg ggaggctgga ctgcgggcac gacttccacg ctggctgcat caagcaatgg      1920
ctggtggtga agaacgtgtg ccccatctgc aagagcaccg cattgaagaa gacctga            1977
```

<210> SEQ ID NO 12
<211> LENGTH: 658
<212> TYPE: PRT
<213> ORGANISM: Zea mays

<400> SEQUENCE: 12

```
Met Gln Gly Gln Arg Asn Ser Met Glu His Phe Ala Asp Val Phe Gly
1               5                   10                  15

Phe Asp Val Ala Ser Ser Ser Gly Asn Pro Val Met Asp Gln Gln Ser
            20                  25                  30

Tyr Trp Asn Asn Val Leu Gly Ser Val Glu Ser His Asn Leu Gln Gly
        35                  40                  45

Tyr Gln Met Ala His Ser Asp Ala Ala Met Pro Tyr Gly Asn Glu Pro
    50                  55                  60

Gln Gln Asp Gly Thr Phe Leu Gly Phe Trp Glu Ser Gly Glu Ala Ser
65                  70                  75                  80

Ala Ser Gly Ser Ser Asn Asn Ala Lys Thr Glu His Leu Asn Ile Gly
                85                  90                  95

Gly Gly Gly Gly Leu Arg Ile Gly Glu Ser Arg Leu Val Ala Asp Asn
            100                 105                 110

Gly Ile Ser Leu Asp Val Asp Ile Asn Leu Asn Ala Asn Val Asn Asp
        115                 120                 125

Leu Cys Gly Gln Ser Ser Asn Val Asn Cys Ala Ser Gln Gly Pro Glu
130                 135                 140

Gln Tyr Cys Gly Ser Asp Arg Asn Ala Ile Asn Ser Gln Pro Thr Asp
145                 150                 155                 160

Leu Gly Leu His Pro Phe Arg Thr Phe Leu Leu Asp Ala Gln Ala
                165                 170                 175

Glu Ser Phe Thr Leu Asn Pro Ser Glu Asn Pro Leu Gly Asp Phe Ser
            180                 185                 190

Ser Met Gln Glu Ser Ile Asp Gln Arg Pro Gly Gly Ser Leu Asp Gly
        195                 200                 205

Arg Arg Leu Ala Cys Lys Arg Lys Asn Ile Glu Gly Ala Asn Gly Gln
    210                 215                 220

Ser Ser Ala Gly Ala Ser Thr Ser Phe Pro His Arg Asn Asp Asn Ala
225                 230                 235                 240

Phe His Asn Ile Ala Ser Ser Ser Tyr Asn Pro Ala Pro Ile Arg Asn
                245                 250                 255

Ser Ser Ser Pro Lys Cys Leu Pro Val Pro Ser Ser Ile Glu Asp Gln
            260                 265                 270

Leu Pro Arg Tyr Gly Thr Asn Val Gly Leu Ser Ala Gly Thr Tyr Asp
        275                 280                 285

Leu His Gly Gly Val Asn Asn Ala Val Asn Ser Gln Arg Ser Phe Arg
    290                 295                 300

Ala Arg Thr Thr Thr Ser Gln Gln Val Ala Pro Cys Ser Val Trp Pro
305                 310                 315                 320
```

Ser Ser Asn Ala Ile Arg Leu Ser Asn Ser Trp Asn His Gln Pro Pro
              325                 330                 335

His Phe Gln Ser Ala Phe Asp Asp Pro Gln Glu Val Ile Pro Val Val
        340                 345                 350

Ser Ser Leu Asn Leu Gln Tyr Gln His Pro Met Asn Val Pro Gly Val
        355                 360                 365

Pro Gln Ala Ala Asn Arg Phe Thr Asp His Gly Ala Ser Ser Ser Arg
370                 375                 380

Ala Gly Ser Leu Glu Asn Arg Ile Ile Gly Glu Glu Val Pro Arg
385                 390                 395                 400

Arg Tyr Ala Ala Pro Thr Asn Tyr Ser Asp Leu Val Pro Pro Ala
                405                 410                 415

Val Asp Leu Arg Arg Leu Val Pro Glu Pro Phe Asn Trp Ser Ser Asp
        420                 425                 430

Val Arg Gly Thr Ala Ile Ser Gly Ser Ile Ile Pro Pro Val Ser Arg
        435                 440                 445

Thr Asn Asn Ser Ser Thr Val Asn Pro Pro Ala Gly Phe Asn His Gln
        450                 455                 460

Asn Leu Thr Arg Arg His Pro Arg Asn Leu Ser Glu Glu Ile Gly Arg
465                 470                 475                 480

Leu Ser Gly Ala Leu Arg Gly His Gln Pro Pro Arg Leu Arg Ser Gly
                485                 490                 495

Phe Leu Leu Glu Arg Gln Gly Asp Gly Val Trp Gly Val Pro Leu Ser
                500                 505                 510

Thr Arg Gly Arg Glu Gly Arg Arg Leu Met Glu Ile Arg Asn Ala Leu
        515                 520                 525

Glu Met Ile Gln Arg Gly Glu Asn Val Arg Leu Glu Ser Ile Phe Tyr
530                 535                 540

Gly Gly Leu Asp Ile His Asp Arg His Arg Asp Met Arg Leu Asp Ile
545                 550                 555                 560

Asp Asn Met Ser Tyr Glu Glu Leu Leu Ala Leu Glu Glu Arg Ile Gly
                565                 570                 575

Asn Val Ser Thr Gly Leu Ser Glu Glu Ala Val Ile Arg Leu Leu Lys
                580                 585                 590

Gln Arg Lys Phe Ser Ser Trp Thr Leu Lys Ala Ser Leu Asp Pro Glu
        595                 600                 605

Pro Cys Cys Ile Cys Gln Glu Glu Tyr Ala Asp Gly Asp Asp Leu Gly
        610                 615                 620

Arg Leu Asp Cys Gly His Asp Phe His Ala Gly Cys Ile Lys Gln Trp
625                 630                 635                 640

Leu Val Val Lys Asn Val Cys Pro Ile Cys Lys Ser Thr Ala Leu Lys
                645                 650                 655

Lys Thr

<210> SEQ ID NO 13
<211> LENGTH: 408
<212> TYPE: DNA
<213> ORGANISM: Artificial
<220> FEATURE:
<223> OTHER INFORMATION: Engineered miRNA precursor

<400> SEQUENCE: 13
ggcagagccg tgcccgtctc atccctgcc cgtgcaagca gctaggtagg acgatttgag    60
cgtggtgtta ggccgaaccg ctgaaggaag attgctccac tgttgactgc attaaatttc   120

-continued

```
gaggatggcg tccaaatgta ttgcttatat tcagcaatat aatgttcgga cgccataagc    180
gaaatttaat atagtcgata gtggaagaac ggtaacatat gtggtttgca gcaggtgagc    240
aggatgggtg tggatgattg aatatctctg ttcagtgttt tcatcatctg actgaacact    300
gaatcagctt gctgacgtta gaggtttcag tttacctaat ttatggtctg tacccatgaa    360
aagtgggaaa aggctgaaga attcgatttc tttctttctt tcaatgtt                 408
```

<210> SEQ ID NO 14
<211> LENGTH: 21
<212> TYPE: DNA
<213> ORGANISM: Artificial
<220> FEATURE:
<223> OTHER INFORMATION: miRNA recognition site

<400> SEQUENCE: 14

```
taaatttcga ggatggcgtc c                                               21
```

<210> SEQ ID NO 15
<211> LENGTH: 391
<212> TYPE: PRT
<213> ORGANISM: Arabidopsis thaliana

<400> SEQUENCE: 15

```
Met Ala Pro Asp Asn Asp His Phe Leu Asp Ser Pro Ser Pro Leu
1               5                   10                  15

Leu Glu Met Arg His His Gln Ser Ala Thr Glu Asn Gly Gly Gly Cys
            20                  25                  30

Gly Glu Ile Val Glu Val Gln Gly Gly His Ile Val Arg Ser Thr Gly
        35                  40                  45

Arg Lys Asp Arg His Ser Lys Val Cys Thr Ala Lys Gly Pro Arg Asp
    50                  55                  60

Arg Arg Val Arg Leu Ser Ala Pro Thr Ala Ile Gln Phe Tyr Asp Val
65                  70                  75                  80

Gln Asp Arg Leu Gly Phe Asp Arg Pro Ser Lys Ala Val Asp Trp Leu
                85                  90                  95

Ile Thr Lys Ala Lys Ser Ala Ile Asp Asp Leu Ala Gln Leu Pro Pro
            100                 105                 110

Trp Asn Pro Ala Asp Thr Leu Arg Gln His Ala Ala Ala Ala Asn
        115                 120                 125

Ala Lys Pro Arg Lys Thr Lys Thr Leu Ile Ser Pro Pro Pro Gln
    130                 135                 140

Pro Glu Glu Thr Glu His His Arg Ile Gly Glu Glu Asp Asn Glu
145                 150                 155                 160

Ser Ser Phe Leu Pro Ala Ser Met Asp Ser Asp Ser Ile Ala Asp Thr
                165                 170                 175

Ile Lys Ser Phe Phe Pro Val Ala Ser Thr Gln Gln Ser Tyr His His
            180                 185                 190

Gln Pro Pro Ser Arg Gly Asn Thr Gln Asn Gln Asp Leu Leu Arg Leu
        195                 200                 205

Ser Leu Gln Ser Phe Gln Asn Gly Pro Pro Phe Pro Asn Gln Thr Glu
    210                 215                 220

Pro Ala Leu Phe Ser Gly Gln Ser Asn Asn Gln Leu Ala Phe Asp Ser
225                 230                 235                 240

Ser Thr Ala Ser Trp Glu Gln Ser His Gln Ser Pro Glu Phe Gly Lys
                245                 250                 255

Ile Gln Arg Leu Val Ser Trp Asn Asn Val Gly Ala Ala Glu Ser Ala
```

```
            260                 265                 270
Gly Ser Thr Gly Gly Phe Val Phe Ala Ser Pro Ser Ser Leu His Pro
        275                 280                 285

Val Tyr Ser Gln Ser Gln Leu Leu Ser Gln Arg Gly Pro Leu Gln Ser
    290                 295                 300

Ile Asn Thr Pro Met Ile Arg Ala Trp Phe Asp Pro His His His
305                 310                 315                 320

His His His Gln Gln Ser Met Thr Thr Asp Asp Leu His His His
                325                 330                 335

Pro Tyr His Ile Pro Pro Gly Ile His Gln Ser Ala Ile Pro Gly Ile
                340                 345                 350

Ala Phe Ala Ser Ser Gly Glu Phe Ser Gly Phe Arg Ile Pro Ala Arg
            355                 360                 365

Phe Gln Gly Glu Gln Glu His Gly Gly Asp Asn Lys Pro Ser Ser
        370                 375                 380

Ala Ser Ser Asp Ser Arg His
385                 390

<210> SEQ ID NO 16
<211> LENGTH: 323
<212> TYPE: PRT
<213> ORGANISM: Arabidopsis thaliana

<400> SEQUENCE: 16

Met Glu Asn Met Gly Asp Ser Ser Ile Gly Pro Gly His Pro His Leu
1               5                   10                  15

Pro Pro Gly Phe Arg Phe His Pro Thr Asp Glu Glu Leu Val Val His
                20                  25                  30

Tyr Leu Lys Lys Lys Ala Ala Ser Val Pro Leu Pro Val Ser Ile Ile
            35                  40                  45

Ala Glu Ile Asp Leu Tyr Lys Phe Asp Pro Trp Glu Leu Pro Ser Lys
        50                  55                  60

Ala Ser Phe Gly Glu His Glu Trp Tyr Phe Phe Ser Pro Arg Asp Arg
65                  70                  75                  80

Lys Tyr Pro Asn Gly Val Arg Pro Asn Arg Ala Ala Thr Ser Gly Tyr
                85                  90                  95

Trp Lys Ala Thr Gly Thr Asp Lys Pro Ile Phe Thr Cys Asn Ser His
            100                 105                 110

Lys Val Gly Val Lys Lys Ala Leu Val Phe Tyr Gly Gly Lys Pro Pro
        115                 120                 125

Lys Gly Ile Lys Thr Asp Trp Ile Met His Glu Tyr Arg Leu Thr Asp
130                 135                 140

Gly Asn Leu Ser Thr Ala Ala Lys Pro Pro Asp Leu Thr Thr Thr Arg
145                 150                 155                 160

Lys Asn Ser Leu Arg Leu Asp Asp Trp Val Leu Cys Arg Ile Tyr Lys
                165                 170                 175

Lys Asn Ser Ser Gln Arg Pro Thr Met Glu Arg Val Leu Leu Arg Glu
            180                 185                 190

Asp Leu Met Glu Gly Met Leu Ser Lys Ser Ser Ala Asn Ser Ser Ser
        195                 200                 205

Thr Ser Val Leu Asp Asn Asn Asp Asn Asn Asx Asn Asn Lys Glu
    210                 215                 220

His Phe Phe Asp Gly Met Val Val Ser Ser Asp Lys Arg Ser Leu Cys
225                 230                 235                 240
```

Gly Gln Tyr Arg Met Gly Asp Glu Ala Ser Gly Ser Ser Ser Phe Gly
              245                 250                 255

Ser Phe Leu Ser Ser Lys Arg Phe His His Thr Gly Asp Leu Asn Asn
            260                 265                 270

Asp Asn Tyr Asn Val Ser Phe Val Ser Met Leu Ser Glu Ile Pro Gln
            275                 280                 285

Ser Ser Gly Phe His Ala Asn Gly Val Met Asp Thr Thr Ser Ser Leu
        290                 295                 300

Ala Asp His Gly Val Leu Arg Gln Ala Phe Gln Leu Pro Asn Met Asn
305                 310                 315                 320

Trp His Ser

<210> SEQ ID NO 17
<211> LENGTH: 663
<212> TYPE: PRT
<213> ORGANISM: Zea mays

<400> SEQUENCE: 17

Met Gln Gly Gln Arg Asn Ser Met Glu His Phe Ala Asp Val Phe Gly
1               5                   10                  15

Phe Asp Val Ala Ser Ser Gly Asn Pro Val Met Asp Gln Gln Ser
            20                  25                  30

Tyr Trp Asn Asn Val Leu Gly Ser Val Glu Ser His Asn Leu Gln Gly
            35                  40                  45

Tyr Gln Met Ala His Ser Asp Ala Met Pro Tyr Gly Asn Glu Pro
    50                  55                  60

Gln Gln Asp Gly Thr Phe Leu Gly Phe Trp Ser Gly Glu Ala Ser
65                  70                  75                  80

Ser Ser Ala Ser Ala Leu Asn Tyr Gly Ser Ser Asn Asn Val Lys Thr
                85                  90                  95

Glu His Leu Asn Ile Gly Gly Gly Gly Leu Arg Ile Gly Glu Ser
            100                 105                 110

Arg Leu Val Ala Asp Asn Gly Ile Ser Leu Asp Val Asp Ile Asn Leu
            115                 120                 125

Asn Ala Asn Val Asn Asp Leu Cys Gly Gln Ser Ser Val Asn Cys
130                 135                 140

Ala Ser Gln Gly Pro Glu Gln Tyr Cys Gly Ser Asp Arg Asn Ala Ile
145                 150                 155                 160

Asn Ser Gln Pro Thr Asp Leu Gly Leu His Pro Phe Arg Thr Phe Leu
                165                 170                 175

Leu Asp Ala Gln Gln Ala Glu Ser Phe Thr Leu Asn Pro Ser Glu Asn
            180                 185                 190

Pro Leu Gly Asp Phe Ser Ser Met Gln Glu Ser Ile Glu Gln Arg Pro
        195                 200                 205

Gly Gly Ser Leu Asp Gly Arg Arg Leu Ala Cys Lys Arg Lys Asn Ile
    210                 215                 220

Glu Gly Ala Asn Gly Gln Ser Ser Ala Gly Ala Ser Thr Ser Phe Pro
225                 230                 235                 240

His Arg Asn Asp Asn Ala Phe His Asn Ile Ala Ser Ser Tyr Asn
                245                 250                 255

Pro Ala Pro Ile Arg Asn Ser Ser Pro Lys Cys Leu Pro Val Pro
            260                 265                 270

Ser Ser Ile Glu Asp Gln Leu Pro Arg Tyr Gly Thr Asn Val Gly Leu
        275                 280                 285

Ser Ala Gly Thr Tyr Asp Leu His Gly Gly Val Asn Asn Ala Val Asn
290                 295                 300

Ser Gln Arg Ser Phe Arg Ala Arg Thr Thr Ser Gln Gln Val Ala
305                 310                 315                 320

Pro Cys Ser Val Trp Pro Ser Ser Asn Ala Ile Arg Leu Ser Asn Ser
                325                 330                 335

Trp Asn His Gln Pro His Phe Gln Ser Ala Phe Asp Asp Pro Gln
                340                 345                 350

Glu Val Ile Pro Val Val Ser Ser Leu Asn Leu Gln Tyr Gln His Pro
                355                 360                 365

Met Asn Val Pro Gly Val Pro Gln Ala Ala Asn Arg Phe Thr Asp His
370                 375                 380

Gly Ala Ser Ser Arg Ala Gly Ser Leu Glu Asn Arg Ile Ile Gly
385                 390                 395                 400

Ser Glu Glu Val Pro Arg Arg Tyr Ala Ala Pro Thr Asn Tyr Ser Asp
                405                 410                 415

Leu Val Pro Pro Ala Val Asp Leu Arg Arg Leu Val Pro Glu Pro
                420                 425                 430

Phe Asn Trp Ser Ser Asp Val Arg Gly Thr Ala Ile Ser Gly Ser Ile
                435                 440                 445

Ile Pro Pro Val Ser Arg Thr Asn Asn Ser Ser Thr Val Asn Pro Pro
450                 455                 460

Ala Gly Phe Asn His Gln Asn Leu Thr Arg Arg His Pro Arg Asn Leu
465                 470                 475                 480

Ser Glu Glu Ile Gly Arg Leu Ser Gly Ala Leu Arg Gly His Gln Pro
                485                 490                 495

Pro Arg Leu Arg Ser Gly Phe Leu Leu Glu Arg Gln Gly Asp Gly Val
                500                 505                 510

Trp Gly Val Pro Leu Ser Thr Arg Gly Arg Glu Gly Arg Arg Leu Met
515                 520                 525

Glu Ile Arg Asn Ala Leu Glu Met Ile Gln Arg Gly Glu Asn Val Arg
530                 535                 540

Leu Glu Ser Ile Phe Tyr Gly Gly Leu Asp Ile His Asp Arg His Arg
545                 550                 555                 560

Asp Met Arg Leu Asp Ile Asp Asn Met Ser Tyr Glu Leu Leu Ala
                565                 570                 575

Leu Glu Glu Arg Ile Gly Asn Val Ser Thr Gly Leu Ser Glu Glu Ala
                580                 585                 590

Val Ile Lys Leu Leu Lys Gln Arg Lys Phe Ser Ser Trp Arg Leu Lys
595                 600                 605

Ala Ser Leu Asp Pro Glu Pro Cys Cys Ile Cys Gln Glu Glu Tyr Val
610                 615                 620

Asp Gly Asp Asp Leu Gly Arg Leu Asp Cys Gly His Asp Phe His Ala
625                 630                 635                 640

Gly Cys Ile Lys Gln Trp Leu Val Val Lys Asn Val Cys Pro Ile Cys
                645                 650                 655

Lys Asn Thr Ala Leu Lys Ala
                660

<210> SEQ ID NO 18
<211> LENGTH: 408
<212> TYPE: DNA
<213> ORGANISM: Oryza sativa

<400> SEQUENCE: 18

```
ggcagagccg tgcccgtctc atccctgcc cgtgcaagca gctaggtagg acgatttgag    60
cgtggtgtta ggccgaaccg ctgaaggaag attgctccac tgttgactgc attaggattc   120
aatccttgct gctaaatgta ttgcttatat tcagcaatat aatgttcagc agcaagaact   180
ggatcttaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggtttcag tttacctaat ttatggtctg tacccatgaa   360
aagtgggaaa aggctgaaga attcgatttc tttctttctt tcaatgtt                408

<210> SEQ ID NO 19
<211> LENGTH: 325
<212> TYPE: DNA
<213> ORGANISM: Oryza sativa

<400> SEQUENCE: 19
ggcagagccg tgcccgtctc atccctgcc cgtgcaagca gctaggtagg acgatttgag    60
cgtggtgtta ggccgaaccg ctgaaggaag attgctccac tgttgactgc attaggattc   120
aatccttgct gctaaatgta ttgcttatat tcagcaatat aatgttcagc agcaagaact   180
ggatcttaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggt                                         325

<210> SEQ ID NO 20
<211> LENGTH: 280
<212> TYPE: DNA
<213> ORGANISM: Oryza sativa

<400> SEQUENCE: 20
ggcagagccg tgcccgtctc atccctgcc cgtgcaagca gctaggtagg acgatttgag    60
cgtggtgtta ggccgaaccg ctgaaggaag attgctccac tgttgactgc attaggattc   120
aatccttgct gctaaatgta ttgcttatat tcagcaatat aatgttcagc agcaagaact   180
ggatcttaat atagtcgata gtggaagaac ggtaacatat gtggtttgca gcaggtgagc   240
aggatgggtg tggatgattg aatatctctg ttcagtgttt                         280

<210> SEQ ID NO 21
<211> LENGTH: 249
<212> TYPE: DNA
<213> ORGANISM: Oryza sativa

<400> SEQUENCE: 21
ggcagagccg tgcccgtctc atccctgcc cgtgcaagca gctaggtagg acgatttgag    60
cgtggtgtta ggccgaaccg ctgaaggaag attgctccac tgttgactgc attaggattc   120
aatccttgct gctaaatgta ttgcttatat tcagcaatat aatgttcagc agcaagaact   180
ggatcttaat atagtcgata gtggaagaac ggtaacatat gtggtttgca gcaggtgagc   240
aggatgggt                                                           249
```